United States Patent
Cardamone et al.

[19]

[11] Patent Number: 5,980,508

[45] Date of Patent: Nov. 9, 1999

[54] CONTROLLED RELEASE DEVICE AND METHOD

[75] Inventors: Michael Cardamone, Thomastown; Herbert William Bentley, Sylvania, both of Australia

[73] Assignee: Controlled Release Technologies Pty Ltd, Victoria, Australia

[21] Appl. No.: 08/750,894

[22] PCT Filed: Jun. 22, 1995

[86] PCT No.: PCT/AU95/00366

§ 371 Date: Apr. 30, 1997

§ 102(e) Date: Apr. 30, 1997

[87] PCT Pub. No.: WO95/35131

PCT Pub. Date: Dec. 28, 1995

[30] Foreign Application Priority Data

Jun. 22, 1994 [AU] Australia ............................... PM 6413
Mar. 21, 1995 [AU] Australia ............................... PN 1866

[51] Int. Cl.$^6$ ..................................................... A61K 9/22
[52] U.S. Cl. ......................................................... 604/890.1
[58] Field of Search ........................... 604/892.1, 890.1, 604/891.1; 424/449, 473

[56] References Cited

U.S. PATENT DOCUMENTS

| | | | |
|---|---|---|---|
| 4,203,440 | 5/1980 | Theeuwes | 128/260 |
| 4,203,441 | 5/1980 | Theeuwes | 128/260 |
| 4,203,442 | 5/1980 | Michaels | 128/260 |
| 4,717,568 | 1/1988 | Eckenhoff et al. | 424/469 |
| 4,976,966 | 12/1990 | Theeuwest et al. | 424/473 |
| 5,011,692 | 4/1991 | Fujioka et al. | 424/426 |
| 5,017,381 | 5/1991 | Maruyama et al. | 424/472 |
| 5,110,597 | 5/1992 | Wong et al. | 424/438 |
| 5,137,727 | 8/1992 | Eckenhoff | 424/422 |
| 5,209,746 | 5/1993 | Balban et al. | 604/892.1 |

FOREIGN PATENT DOCUMENTS

| | | |
|---|---|---|
| 73310/87 | 11/1987 | Australia . |
| 0 246 819 | 11/1998 | European Pat. Off. . |
| 2 206 047 | 12/1988 | United Kingdom . |
| 3 306 046 | 12/1988 | United Kingdom . |
| 2 241 485 | 9/1991 | United Kingdom . |
| 2 243 777 | 11/1991 | United Kingdom . |
| WO 89/06943 | 9/1989 | WIPO . |
| WO 92/16194 | 10/1992 | WIPO . |
| WO 92/17165 | 11/1992 | WIPO . |

*Primary Examiner*—Manuel Mendez
*Attorney, Agent, or Firm*—Joan H. Pauly

[57] ABSTRACT

A device for dispensing one or more active agents, the device including: a housing (112) having an opening; at least one active agent (118) located within the housing; a driving means (124) located within, or at the closed end of the housing, including an expandable material; and one or more permeable fluid conveying passage(s) adapted to convey fluid from outside the housing to the driving means.

38 Claims, 26 Drawing Sheets

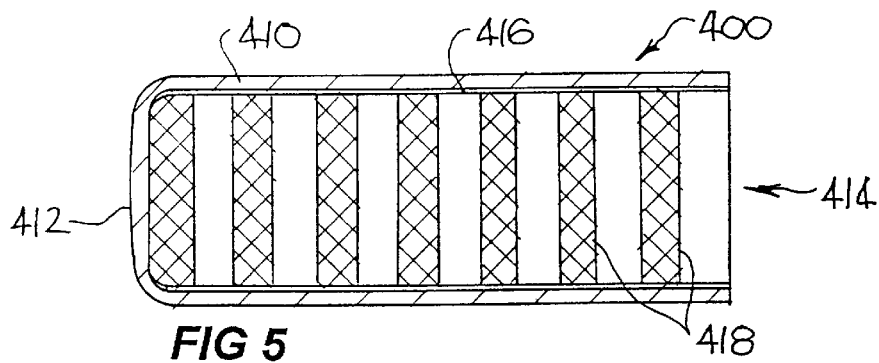
FIG 5
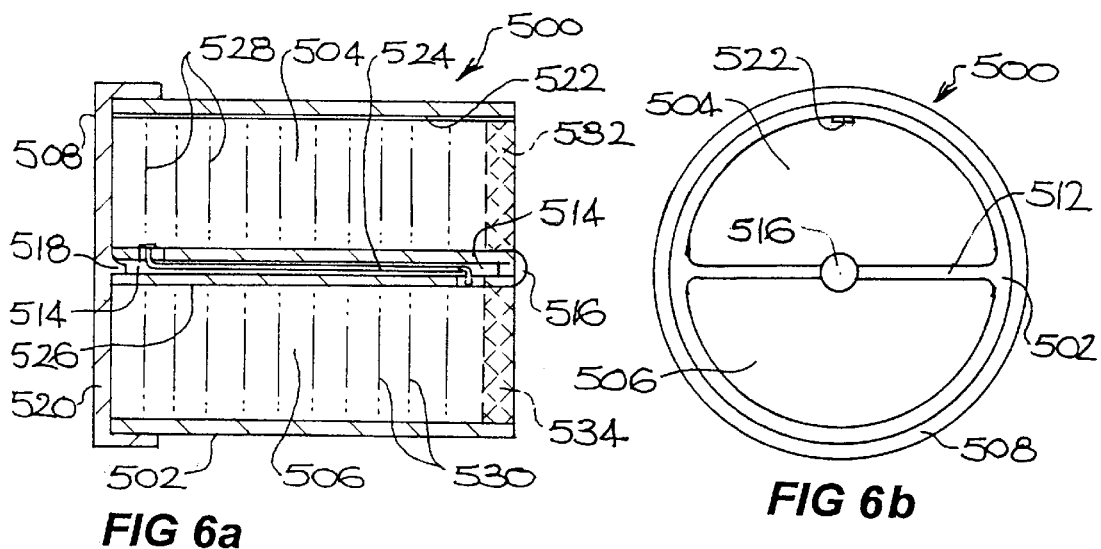
FIG 6a  FIG 6b
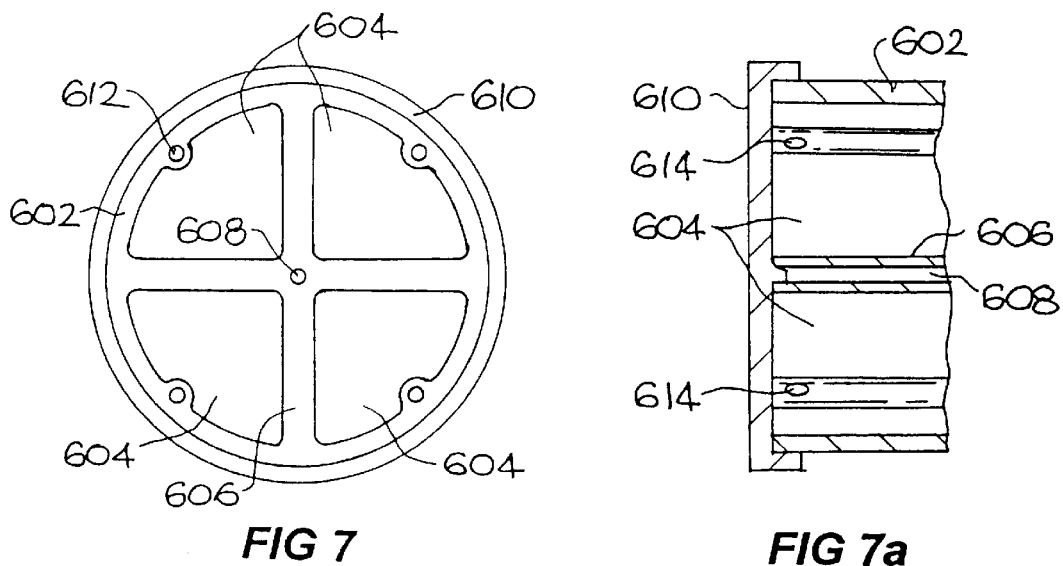
FIG 7  FIG 7a

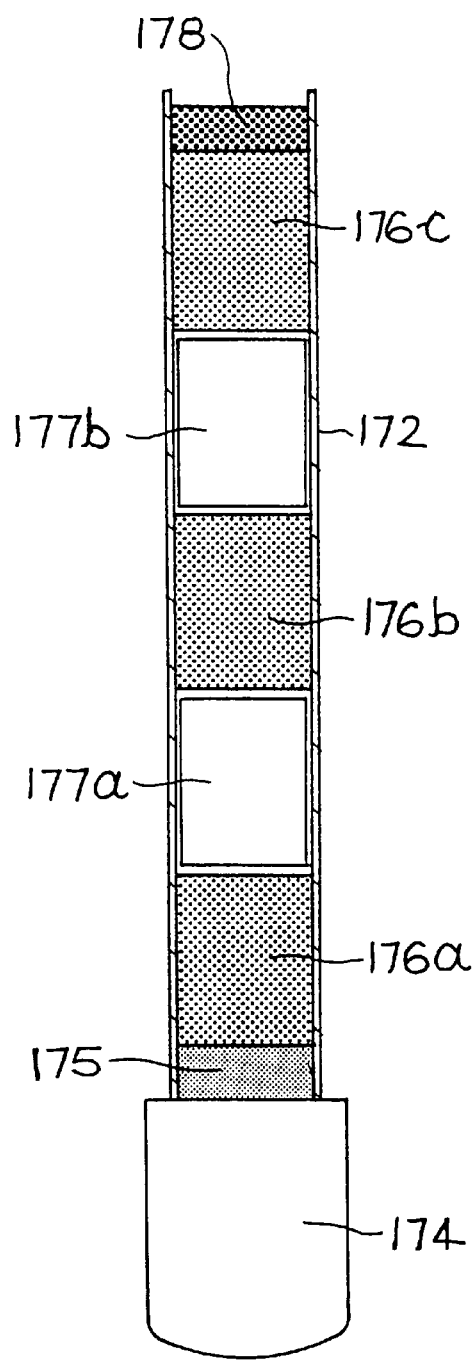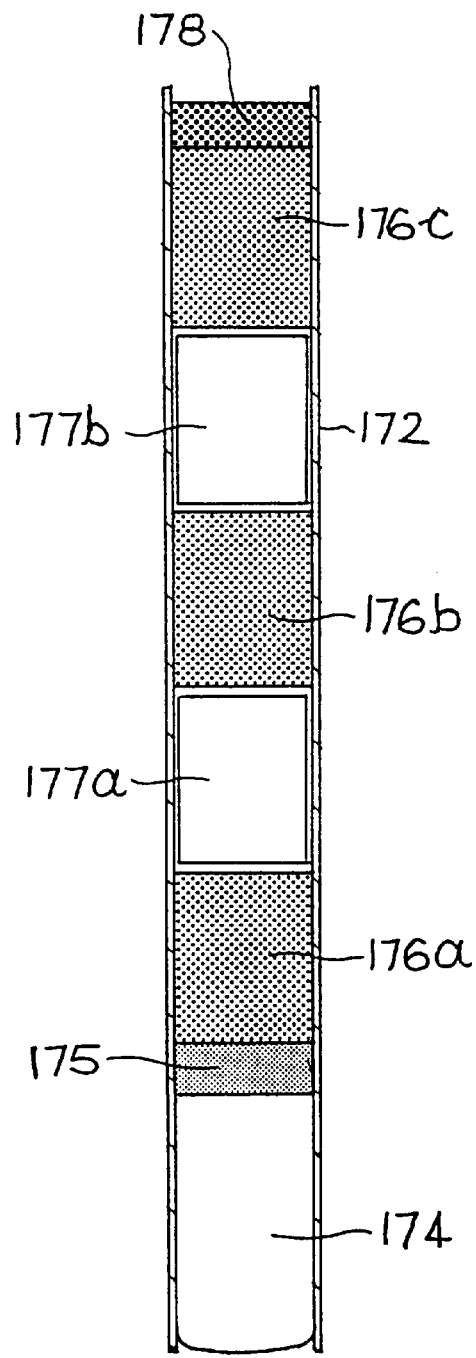
FIG 17a  FIG 17b

CONTROLLED RELEASE DEVICE AND METHOD

FIELD OF INVENTION

The present invention relates to devices and methods for the administration of useful agents, for example bioactive agents, to humans, animals, plants, fish or birds (herein called "the patient"). It has particular, though by no means exclusive, application to the staged delivery of multiple doses of one or more agents at timed intervals over a prolonged period of time and/or to the continuous delivery of one or more agents over a prolonged period of time.

The uses of such methods, devices and capsules are many and varied. For example, controlled-release may be used to maintain the blood-level of a therapeutic agent substantially constant over an extended period of time; it may be used to achieve a predetermined time/concentration profile of an antigen in the blood, an anti-tumour agent in an organ, or an anthelmintic in the gut and/or blood of a patient; or, as required for the administration of some hormones which control reproduction or growth, and are required for the administration of many antigens (e.g. in vaccination), controlled release may be used to achieve pulsatory delivery where multiple doses of a drug are required at predetermined intervals or where an extended dose is to be delivered in a continuous or pulsatory fashion.

For convenience in this specification, the active agent to be delivered, whether it be a hormone, antibiotic, antigen, vitamin, anti-tumour drug, vaccine, cytokine, etc., will be termed a "drug", though it is by no means limited to pharmaceutical compounds, nor to the route of administration (e.g. subcutaneous, intra-muscular, sub-dermal, dermal, intravenous, intra-arterial, peritoneal, etc.).

BACKGROUND OF THE INVENTION

With the development of more and more types of extracted, synthetic or genetically engineered hormone-like substances which are effective at very low levels of concentration, the need for implantable or ingestable controlled-release capsules has grown considerably and many designs for such devices have been proposed. One convenient form of implantable device is an open-ended cylinder or tube of a few millimeters in diameter (so that it can be implanted by the use of a hypodermic syringe) formed from material which is biocompatible but generally impervious to body fluids.

If the sustained release of a single drug dose is desired, the drug is simply mixed with a suitable excipient, loaded into the device and implanted. Whereupon, the action of the body fluids gradually dissolves, disperses or penetrates the excipient and releases the drug over a period of time. If pulsatory delivery is required, the capsule cylinder may be loaded with a succession or 'stack' of alternating 'active' and 'spacer' layers each comprising a suitable excipient, carrier or matrix. Each active layer contains a dose, or a relatively high concentration of the drug(s) to be delivered, while each spacer layer contains no drug(s) or a relatively low concentration thereof. Dissolution, leaching or erosion of each successive layer (by body fluids after implantation) provides the desired pulsatory drug delivery, while the formulation of the excipient of an active layer determines the profile of the corresponding dose, and the formulation of a spacer layer determines the time interval between the doses of the adjacent active layers.

Such known capsules may be divided into those which are 'active' (or 'swellable agent') and those which are 'passive' (or 'un-swellable agent'). In the latter, the timing and rate of release of the drug doses represented by the active layer(s) depends upon the formulation of the excipient(s) and drug(s) employed, given a particular composition of surrounding body fluid. In the former, the layer-stack is pushed or extruded gradually from the open end of the capsule by a 'swellable agent' located at the other—and closed—end of the capsule, so that one layer after another is ejected for dissolution into the body fluids. Thus, the interval between doses—and to some degree, the dose profile as well—is determined by the rate of extrusion as well as the excipient formulation.

A basic form of pulsatory passive capsule is disclosed by U.S. Pat. No. 5,011,692 to Sumitomo. Here a hollow cylindrical casing of impermeable material contains a stack of alternating active and spacer layers in which the excipient is formed by a specially formulated bio-compatible polymer which can be leached or eroded by body fluids. The problem with such a design is that the dose profile and timing of the first layers tends to be quite different to those of the last layers due to the reduced diffusion-rates in a near-empty capsule. The problem is accentuated where long, thin multi-dose capsules are employed. To compensate, the formulation of the layers may be graded along the stack—but at the penalty of greatly increased manufacturing cost. Also, since the innermost layers of such a stack are likely to be highly permeable, the drug in those layers is likely to diffuse from one to another during storage thereby degrading the desired release profile.

An alternative form of passive capsule (e.g. WO9217165 in the name of the Victorian Pharmacy College) involves the encapsulation of a drug-excipient mixture with an erodable (but initially) impervious coating which gradually degrades in vivo to release the drug. But such an approach is notoriously non-linear unless the distribution of the drug within the excipient is carefully graded or many micro-capsules with different coatings are separately implanted or included in the one implanted macro-capsule.

Another form of passive capsule (exemplified by United Kingdom patent 2,241,485 to NRDC and U.S. Pat. No. 5,137,727 to Alza) uses a casing having one or more chambers connected in series with one another and to the external environment by apertures which are stopped with bioerodable plugs, each chamber containing a separate dose of the drug to be delivered. Reliance is thus placed upon the characteristics of the plug(s) to ensuring the desired timing of the dose(s), while the profile of the dose itself is—as before—determined by the formulation of its excipient and the drug. However, the release profile of the doses in the inner chamber will differ even more radically from those in the outer chambers than is the case with a layered-stack capsule.

In another form of chambered passive capsule, (e.g. NRDC United Kingdom patent 2,243,777) the connection between a single drug-containing chamber and the surrounding fluid of the body is restricted by the tube, the outer end of which is closed with a soluble plug. Such a capsule may be satisfactory where the delayed release of a sustained single dose is required, but its design obviously not suited to pulsatory delivery.

An alternative approach to the linearity problem is to employ a capsule casing which is formulated so that it erodes away only at the edge—that is, at the open end—to gradually successive expose active and spacer layers of the stack. However, the formulation of a casing of this type is extremely difficult and, to the applicant's knowledge, has not been achieved with practical success.

The active or pump capsule avoids the inherent linearity problem of the passive capsule by gradually pushing the layer-stack out of the open end of the capsule so that each successive layer becomes the top or outermost layer thereby ensuring that its release profile is essentially the same as that of the previous (and now dissolved or dispersed) layers. Also, in this way, the timing of the release of each dose is now determined largely by rate of extrusion (i.e. by the swellable agent design) rather than solely by the formulation and thickness if the spacer layer(s). The pump may be physical (e.g. driven mechanically, electro-mechanically or by gas pressure), physio-chemical (e.g. driven by an expanding hydrogel which imbibes fluid from the environment) or osmotic (e.g. driven by an expanding solute which imbibes a solvent—usually water—from the environment through an ion-selective membrane). The latter two forms of pump are preferred because of their relatively low cost and small size, because they generate a more uniform force over their stroke (in comparison with most spring or gas-operated swellable agents) and because their materials can be more readily made biocompatible. A range of osmotic pumps for this purpose are disclosed in U.S. Pat. Nos. 4,203,440, 4,203,441 and 4,203,442 to Alza.

The active devices of the prior art are designed to provide a constant rate of extrusion with the gradual diminution of swellable agent pressure being offset by the lowered friction of a shorter stack as delivery progresses. This allows the timing of the dose(s) to be made proportional to the thickness of the corresponding layer(s). This problem is said to be addressed by Merck in its Australian patent application 73310/87 where it is proposed that the spacer layers of a multi-dose active capsule should employ an expanding excipient formulation. While it is suggested the effective length of the capsule is made much greater than its physical length in this way, a little thought will show that the inclusion of expanding spacer layers must have the effect of increasing the average extrusion rate of material from the capsule, thus effectively shortening its effective length (compared to an equivalent capsule with non-expanding layers).

OBJECTIVES OF THE INVENTION

It is therefore an object of the present invention to overcome, or at least alleviate, one or more of the difficulties or deficiencies of the prior art devices indicated above.

Outline of the Invention

The present invention provides a device for dispensing one or more active agents, the device including:

a housing having an opening;

at least one active agent located within the housing;

a driving means located within, or at the closed end of, the housing, the driving means including an expandable material; and one or more permeable fluid conveying passage(s) adapted to convey fluid from outside the housing to the driving means.

By permeable fluid conveying passages, we mean one or more passages that allow restricted but controlled conveyance of fluid, such as body fluid, to the expandable material, but not so restricted as to provide semi-permeable flow.

For example, applicants have now demonstrated infiltration of blood vessels occurs into the permeable fluid conveying passages, unlike semi-permeable systems (see FIGS. 1A and 1B).

The driving means may include an expandable layer of a passive or active device and/or a liquid imbibing swellable agent of an active device.

The device may include more than one driving means.

The active agent may be a biologically active agent used in medical, including veterinary, applications and in agriculture, such as with plants, as well as other areas. The device of the invention may also have industrial applications.

The expressions "active agent" and "drug" are used interchangeably and are used in this document broadly and may include any compound, composition of matter or mixture thereof that can be delivered from the system to produce a useful result. The active agent or drug may include as examples without limitation, macromolecular bioactive agents of biological origin, inorganic and organic. This includes but is not limited to pesticides, herbicides, germicides, biocides, algaecides, rodenticides, fungicides, insecticides, antioxidants, plant growth promoters, plant growth inhibitors, perservatives, antiperservatives, disinfectants, sterilisation agents, catalysts, chemical reactants, chemical products, fermentation agents, foods, food supplements, nutrients, cosmetics, drugs, vitamins, sex sterilants, fertility promoters, fertility inhibitors, air purifiers, micro-organism attenuators, and other environmental agents.

Active agents and drugs may also include any physiologically and pharmacologically active substances that produce a localised or systemic effect(s) in animals, including but not limited to warm blooded mammals, humans, primates, avians, domestic household, sport, zoo, wild and/or farm animals.

Organic and inorganic active agents may include but are not limited to acetylcholine esterase inhibitors, aminoglycocides, angiotensin converting enzyme inhibitors, antiarrhythmics, antibacterial agents, antibiotics, anticancer agents, antidepressants, antidiabetics, antiepileptics, antiviral agents, antihistamines, antihypertensives, antinauseants, antiprostaglandins, antirheumatics, antiseptics, barbiturates, beta-blockers, betalactamase inhibitors, calcium channel blockers, cardiac glycosides, cephalosporins, immune reagents, immunostimulators, immuno-suppressives, liposaccharide complexing agents, methylxanthines, minerals, O-beta-hydroxyethylated rutins, propxyphenes, salicyclates, tetracyclin compounds, vasodilators, acetaminiophen, acetazolamide, acetophenetidin, achromycine hydrochloride, bendofluazide, benzthiozide, betamethasone, calcium and salts, thereof including, leucovorin calcium, carbamazepine, clindamycin, chlorpropamide, chlorothalidone, chlorothiazide, clofibrate, cortisone acetate, cyclopenthiazide, dexamethazone, dextroamphetamine sulphate, diclofenac sodium, digoxin, dimethindene and salts thereof, diprophylline, disopyramide and salts thereof, dipyrone, doxycycline, fenbufen, fenoprofen, ferrous fumarate, flurbiprofen, frusemide, furosemide, glibenclamide, haloperidol, hydralazine, hydrochloride hydrochlorothiazide, hydroflumethiazide ibuprofen, indomethacin, indoprofen, iron salts, kanamycin, ketoprofen, L-Dopa, lithium salts, metaclopramide, methazolamide, methotrexate, fluoro-uracil, methotrexate sodium, methyl Dopa, metronidazole, minocyclin hydrochloride, mofebutazone, morphine, naproxen, nifedipine, oxyphenbutazone, penicillin, peridinol and salts thereof, phenylbutazone, phenobarbital, phenylpropanolamine, phenytoin, pindolol, piroxicam, pirprofen, potassium chloride, prazosin, propanolol, proxyphilline, pyrvinium emboate, quinidine, reserpine, salicylamide, salicyl salicyclic acid, sodium fluoride, spironolactone, sulfadiazine, sulfamerazine, tetracyclin compounds, tolbutamide, trihexylphenidyl hydrochloride, triethoprim, valproic acid, vancomycin, zoxazolamine, carbonic anhydrase inhibitors, anti-glaucoma agents, benzalkonium chloride, benzocaine, amilorid, those materials that act upon the central nervous system such as hypnotics, sedatives, psychic energizers, tranquillisers, anticonvulsants, muscle relaxants, anti-parkinson agents, analgesics, steroidal anti-inflammatories, anti autoimmune agents, local and systemic anaesthetics, hormonal agents such as contraceptives, sympathomimetrics, parasympathomimetrics, lipid regulating agents, anti-androgenics, antiparasitics, neoplastics, anti-AIDS agents, mutagens, teratogens, hypoglycaemic, nutritionals, fats, ophthalmics, otolaryngolmics, electrolytes, diagnostic agents, diuretics, nonsteroidal anti-inflammatories such as aspirin, ibuprofen, antihistamines such as diphenhydramine, chlomethazine, clemastine, hydroxyzine, terfenadine promethazine, astemizole, loratadine, mast cell stabilisers such as cromolyn sodium, bronchodilators such as metaproterol sulphate, isoetharine hydrochloride, theophylline, albuterol, epinedrine, norepinedrine, adrenaline, noradrenaline, corticosteroids such as prednisone, prednisolone, hydrocortisone, cortisone acetate, flunisolide and triamincinolone acetate, anti cholesterol agents, oestradiol, progesterones, testosterone, amino acids, thyroxine, peptides such as enkephalins, histamine, fatty acids and fatty acid derivatives such as prostaglandins E2 etc., inositol phosphates, gamma-aminobutyric acid, ketone bodies, acetylcholine, and mixtures thereof.

Macromolecular bioactive agents include but are not limited to protein, DNA, carbohydrates and mixtures thereof. This may include immunoglobulins G, M, A, D and E and their fragments and sub-chains, hormones such as insulin, somatotrophins, growth hormones, somatomedins, erythromycin, adrenocorticotropic hormone (ACTH), parahormone, Follicle stimulating hormone, inhibin, renin, Leuteinizing hormone, Thyroid stimulating hormone, hypothalamic releasing hormones such as LH releasing factor, TSH releasing factor, gastrointestinal hormones such as gastrin, cholecystokinin, etc., vasopressin (ADH), somatostatin, immunomodulators, immunostimulators and immunoinhibitors such as cytokines including Interferons alpha beta, gamma, etc. and Interleukins 1, 2, 3, 4, etc., tumour necrosis factor alpha, beta, etc., colony stimulating factors (CSF) and growth factors such as Granulocyte CSF Macrophage CSF, Granulocyte-Macrophage CSF, Epidermal Growth Factor, Fibroblast Growth Factor, Nerve Growth Factors, cell chemotactic factors, antihaemophilic factors such as Factor VIII, surface receptors and co-receptors such as CD 1, 2, 3, 4 etc., live attenuated vaccines, killed, inactivated vaccines such as chemically inactivated allergenic extracts such as formalinised toxoided cloistridial vaccines, recombinant sub-unit vaccines, vaccines with or without adjuvants such as aluminium hydroxide, alhydrogel, tyrosine, polytyrosine, dimethylglycine, muramyl dipeptide, mineral oils, detergents, surfactants including but not limited to nonionic block polymer surfactants such as polyoxypropylene, polyoxyethylene, pluronic, saponin, immunomodulators, immunostimulators and immunoinhibitors, allergen source material, allergen extracts, denatured immunoglobulin receptors, and mixtures thereof.

The active agent may be dispensed from the device as a solid, liquid or gas. The active agent may be dispersed in a slurry, concentrated liquid and/or a tablet.

The delivery device of the present invention is particularly suited to the delivery of hormones, such as growth hormone, cytokines and vaccines such as recombinant vaccines. The device of the invention may be adapted to provide pulsatile release, for example, to mimic a circadian pattern of in-vivo release, or continuous release.

Recent progress in the field of controlled drug delivery has resulted in the development of novel techniques and materials which may benefit the production of improved vaccines. Antigen delivery vehicles such as liposomes, microspheres and microcapsules offer the potential to increase antigen stability and immunogenicity, resulting in enhanced or prolonged immune responses or the ability to reduce the amount of antigen required and/or eliminate the need for the use of adjuvants (1). In addition, the form of the antigen may be modified, resulting in induction of the most appropriate protective immune response or allowing delivery by previously unacceptable routes, such as oral administration (2). Appropriate delivery systems would also enhance the activity of recombinant cytokines, administered as alternatives to the harsh chemical adjuvants in current use (3). Studies of such systems for antigen modification have not as yet removed the requirement for multiple administration of vaccine antigens. The device of the present invention may be in the form of an implantable device for the continuous or pulsatile release of antigens and other veterinary pharmaceuticals such as growth hormones, anthelmintics and antibiotics. This device offers the potential for multiple or continuous dosing of a bioactive agent such as an antigen, eliminating the need for repeated handling of subjects and offering significant advantages to livestock industries.

The active material may be an antigen with or without a adjuvant.

The active material may be incorporated into one or more layers of a biocompatible matrix which may include one or more expandable or non-expandable layers.

The active material may take any convenient dosage form. The active material may be combined with conventional excipients and introduced into the device in the form of a powder, solution or dispersion or may be in the form of tablets. The composition may include a lubricant to promote unimpeded movement along the device housing.

The device may be adapted to dispense single or multi-doses of active agent(s). The device may be adapted for staged delivery of multiple doses of one or more agents at timed intervals over prolonged periods, and/or continuous delivery of one or more agents over prolonged periods.

The device may be an implantable or ingestable device.

The device may have a multiplicity of layers arranged lengthwise in the housing with one or more layers being an expandable or nonexpandable layer and one or more layers containing the active agent.

The device may be in the form of a capsule. The housing may be elongated and may be of any suitable cross-section with a generally circular cross-section being preferred.

The device may be in the form of a miniaturised implant which may be adapted for delivery by, for example, a handheld gun.

Optionally, the opening of the device may be closed by occlusion means formed of a material which is discharged, leached or eroded by the environment in which the device is to be used. The occlusion means may be in the form of a plug. The length or size of the plug can be used to regulate the timing of release of the first layer from the capsule.

Preferably the housing is formed at least in part from a substantially fluid impervious material. More preferably, the active agent is located within a substantially fluid impermeable housing.

The hydrophilic/hydrophobic nature of the inner surface of the housing may be selected or altered so as to alter the release profile. An increase in hydrophilicity of the inner surface increases the ingress of fluids such as water.

The housing may be formed from a substantially liquid impermeable polymer such as non-porous polyethylene (including high density polyethylene (HDPE) and ultra high molecular weight polyethylene (UHMWPE), polycarbonate, polypropylene, polyvinyl chloride, polytetrafluoroethylene (PTFE), polyvinylidene fluoride (PVDF) polyvinylacetate, polystyrene, ethylene vinylacetate, nylon, polyimide, polyetheretherketone (PEEK), polyurethane, fluoroethylenepropylene (FEP) and combinations thereof.

The polymer may be a polyhydroxy alkanoate, commonly known as "Biopol".

The polymer may be an elastomer such as silicone rubber, polysiloxane, polybutadiene or polyisoprene. The polymer may be biodegradable such as poly(lactic acid), poly (glycolic acid) poly(alkyl 2-cyanoacrylates), polyanhydrides and polyorthoesters, or bioerodible such as polylactideglycolide copolymers, and derivatives thereof, non-peptide polyaminoacids, polyiminocarbonates, poly alpha amino acids, polyalkyl-cyano-acrylate, polyphosphazenes or acyloxymethyl poly aspartate and polyglutamate copolymers and mixtures thereof. An adhesive may be used in the construction of the device. Examples of suitable adhesives are polyisobutylenes, polyacrylates and silicones. The polymeric material may be coated to improve its biocompatibility.

The driving means may be a water imbibing material of a swellable agent. In the case of swellable agents based on expandable material, such as swellable hydrophilic polymers or hydrogels, no permeable membrane is required. Examples of hydrogels are polyacrylates such as poly (hydroxyalkyl methacrylates), polyvinyl alcohol, poly(N-vinyl-2-pyrrolidone), poly(vinyl acetate), poly (hydroxyethyl methacrylate), alginates and polyacrylamide.

Natural polymers, such as cellulose acetate phthalate, hydroxypropyl cellulose, carboxymethyl cellulose, ethyl cellulose, methyl cellulose, collagen, zein, gelatin, agarose, DEAE, Sephadex T, natural rubber, guar gum, gum agar, curdlan or other schleroglucans, or hydroxymethyl cellulose or albumin are further examples of expanding gels or swelling agents which may be used as driving mechanisms, matrix bases and/or coating excipient material.

The outlet(s) from the permeable fluid conveying passage (s) may be located at any position along the device housing. For example, where the device includes a swellable agent located at one end of the housing, the outlets of the permeable fluid conveying passage(s) may be located at that end adjacent the expandable material. Where the device includes one or more layers of expandable material, the outlet of the fluid conveying passage(s) may be located adjacent one or more of the expandable layers.

An advantage of the device of the present invention is that it avoids the need to incorporate a permeable membrane in the housing of the device, thus allowing for a more robust device. Moreover in a preferred embodiment of the invention, the active agent is protected from direct exposure to the external environment by the substantially fluid impermeable housing until the active agent is dispensed from the device.

We have found that one particularly effective form of permeable fluid conveying passage(s) is one or more capillary means.

Accordingly, in a first preferred embodiment of the invention, there is provided a dispensing device for dispensing one or more active agents, the device including:

housing having an opening;

at least one active agent located within the housing;

a driving means located within or at the closed end of the housing, the driving means including an expandable material; and one or more capillary passages adapted to convey fluid from outside the housing to the driving means.

This embodiment is based upon the realisation that the above objects can be achieved by use of one or more capillary passages to convey body fluid in a restricted but controlled manner to driving means such as an expandable excipient layer(s) of a passive or active capsule and/or to the liquid-imbibing swellable agent of an active capsule. Many benefits can result from the application of this principle to both passive and active devices and to both single and multiple-dose capsules.

If the expansion (by capillary flow) of each layer in a multi-layer passive device is substantial relative to the length of the capsule, much of the linearity problem of prior art passive devices may be overcome. If each layer can be expanded in sequence (as it becomes the outermost layer), the desired dose pattern or sequence can be obtained.

Similarly, if each successive layer of a multi-layer active device is expanded in a controlled manner by capillary flow as it reaches the end of the device, the expansion required by the driving means needed for a desired dose pattern will be relatively small.

Preferably, each active or expandable layer (and preferably each layer) may be formed with a protective skin or coating. The skin or coating may be relatively impervious to body fluid so that, at least the initial stages of expansion are caused and controlled by capillary flow of body fluid to the edge of the layer.

Alternatively the protective skin or coating may be body fluid pervious or soluble, e.g. a coating such as a fat. e.g. magnesium monostearate or castor oil that may be enzymatically removed subsequent to release, to protect or retain the bioactive layer while it is still in the capsule.

Further, by feeding water to a water-imbibing swellable element (or layer) via a capillary passage, the flow of water can be controlled in a variety of advantageous ways. First, the rate of flow of water can be reduced in a reliable manner by adjusting the length of the capillary, its cross-section and/or the number of parallel capillaries feeding the swellable agent (or layer). Second, by arranging the inlet of a capillary inside or close to the open end of the device, the water concentration-gradient across the ends of the capillary will be reduced in synchronism with the dissolution of the layers thereby providing a form of negative feedback in the water flow to the swellable agent (or layer). This effect can be enhanced by forming a shield-tube, of larger diameter than the internal diameter of the device, around the outer end of the device, and arranging the inlet(s) of the capillary (or capillaries) in the thickness of the wall of the device.

Thirdly the hydrogel also provides a concentration gradient that protects the wetting of the layers because even though it imbibes liquid to the driving mechanism it attracts water away from the layers as it expands.

In this context, a capillary passage is one which is many times longer than it is wide, in which the internal surface(s) may be hydrophilic and in which the surface tension of a water-air interface is sufficient to draw water into the passage. Thus, while the rate of water (or body fluid) flow through the capillary passage is low (because of the small cross-section), it is facilitated by surface-tension effects and augmented by the concentration gradient of water in the fluid along the passage.

One or more longitudinally extending capillary passages may be formed by extrusion in the thickness of the wall of the device or within one or more ribs or webs formed in the device. Normally, the casing of the device will be formed from a hydrophobic biocompatible hydrophobic material and the internal walls of the capillaries will be etched or otherwise treated (e.g. by grafting a different polymer thereon) to render them hydrophilic. Furthermore, the capillary passages may include hydrophilic fibrous, granular or mat-form or molecular wick material which facilitates the transport of water and aqueous solutions therethrough. These materials can be formed in situ by extrusion, deposition, polymerisation or sintering, or they can be preformed and then separately inserted into the capillaries.

One or more capillary channels may be formed on the inner surface of a device in the form of a tubular capsule device by moulding, extrusion as a laminate, printing, coating or grafting operations. These channels may be covered and enclosed with a layer of impermeable material so that they are adapted to convey water only to the end bearing the swellable agent, for example; they may be left uncovered so that their inner faces abut the edges of all the excipient layer(s) when the capsule is filled, or so that they abut the edges of only the outermost layer(s); or, selected portions of the capillaries may be covered to shield them from selected layers—the active layers, for example.

Edge wicks of this type can be used in both active and passive capsules and in pulsatile or continuous release systems. For example, an active pulsatile release capsule may have its swellable agent fed with water in the conventional manner via a suitable permeable membrane or by a dedicated capillary (as indicated above) so that the stack of layers is pushed steadily out of the open end of the capsule. But, in this case, each spacer layer (or each active layer) may be formulated to expand when supplied with moisture, and, a short wick may be formed on the inside of the outer end of the casing so as to contact (and feed moisture to) the edge of each expandable layer as it reaches the open end of the device in its turn.

In a passive pulsatile release capsule, for example, a constrained edge-wick may extend the full length of the inner surface of the capsule wall so that it contacts the edges of all the layers of a stack loaded into the capsule. After implantation, moisture will be fed by the wick to the first absorbent and expandable layer causing it to expand and push the preceding active layer from the capsule. By ensuring that the capacity of the wick to deliver water to each expanding layer is substantially less than the capacity of the layer to absorb water, little moisture will be conveyed by the wick to the next expanding layer until the first is nearly saturated and fully expanded. Thus, the expandable layers are activated in sequence and a pulsatory delivery of active material effected. Again the negative feedback effect indicated above may be employed to advantage to limit the flow of water along the wick (in a passive or active capsule) until the outermost layer has dissolved and dispersed.

To assist in spreading the moisture to the desired layer, the 'wick-tracks' on the inner surface of, for example, a pulsatile release capsule may be formed by 'printing' a broad circumferential capillary band opposite each expandable active layer and by joining each band to the next with only a narrow axial capillary channel. Alternatively, the bands may be opposite expandable spacer layers which each (in turn) then acts as a swellable agent which drives the outermost active layer forward and, perhaps, causing its break-up. In the latter case, each active layer may have an outer impermeable skin which is ruptured by the expansion of the adjacent inner spacer layer. Once this pair of layers have dissolved or become saturated with body fluid, the next capillary channel may convey liquid to the next expanding layer.

It will be appreciated that, in the arrangement outlined in the above paragraph, the capillary tracks need not be enclosed or isolated from the edges of the layers. They can be formed as wick-lines or tracks on the internal surface of the capsule wall and may contact the edges of all layers, though the area of contact with each spacer layer may be different from that with each active layer, as indicated above.

The capillary means may be extruded, intertwined or woven fibrous material in the form of a rope, cord or the like, the spacing between the fibres forming the capillary passages. The fibres may be formed from a polymeric material. The polymeric material may be hydrophilic or hydrophobic with the surface thereof being treated so as to be hydrophilic. For example, the surface of the hydrophobic material may be coated with a hydrophilic material by grafting a hydrophilic monomer such as acrylic acid onto the surface of the fibre. The polymer fibre may be formed from polyethylene (including high density polyethylene (HDPE) and ultra high molecular weight polyethylene (UHMWPE)), polyetheretherketone, polyimide, PTFE, PDVF, polypropylene, or FEP.

A device may have multiple parallel bores, each filled with a stack or layers, each bore/stack acting as a passive or an active sub-device. The sub-devices may be arranged to operate in parallel or in series, series operation offering the substantial advantage of multiplying the effective length of the device without increasing its physical length. Where multiple active sub-devices are employed, they may be driven in parallel by separate expandable agents fed from the same or different capillaries, or by the same expandable agent.

A further preferred form of the invention is one in which the permeable fluid conveying passage(s) is a plurality of pores which admit passage of fluid from outside the housing to the driving means.

Accordingly, in a second embodiment, the present invention provides a device for dispensing one or more active agents, the device including:

a housing having an opening and being formed at least in part from a substantially liquid impervious material;

at least one active agent located within the liquid impervious housing;

a driving means located within, or at the closed end of, the housing, the driving means including an expandable material;

said housing including a portion having a plurality of pores formed therein to convey fluid from outside the housing to the driving means.

The plurality of pores may be provided in the form of a porous material such as a porous polymer. The porous polymer may form part of the housing of the device. Alternatively the pores may be in the form of small diameter holes formed by, for example, perforating a portion of the housing.

The degree of porosity of the porous material may be selected so as to obtain the rate of release desired.

The porosity may be provided by a porous plug, cover or cap associated with the body of the housing. The porosity may be provided by a porous inner plug.

The porous polymer may be porous polyethylene although other porous polymers may be used.

The flow rate characteristics of the porous body may be adjusted by selecting characteristics such as polymer type, hydrophobicity, hydrophilicity and the dimensions of the pores.

In one form, the housing of the device may include a water impermeable section with an open end and a porous section fabricated from a porous polymer forming a closed end of the device and surrounding an expandable driving system such as a hydrogel swellable agent.

The pores may be located at one or more positions along the length of the housing particularly where there are a plurality of expandable layers located along the housing.

The device of the present invention may be a combination of the devices defined in the first and second preferred forms of the invention.

Accordingly in a further embodiment of the present invention the device comprises a cylindrical casing formed from a non-porous polymer closed at one end by a Loctite Prism™ adhesive or a cyano-acrylic ester based adhesive. This arrangement is suitable for the formation of a passive device in which a multiplicity of layers is arranged lengthwise inside the housing substantially filling the inside cross-section of the housing and where at least one of the multiplicity of layers is an expandable material. When placed in an environmental fluid, the fluid diffuses into the device between the outside periphery of the layers and the internal surface of the non-porous cylinder. The rate of diffusion of fluid into the device may be adjusted by varying the hydrophilicity or hydrophobicity of the inner surface of the non-porous polymer, for example by surface treatment such as grafting with a hydrophilic polymer.

In a further embodiment of the device of the invention the housing of the device is formed from a cylindrical body formed from a non-porous polymer closed at one end by means of a porous polymer plug through which fluid may flow to a swellable agent.

Alternatively, the porous plug may be integral with the remainder of the housing. For example, the device may be constructed from a single rod that is porous at one end and non-porous at the other. A hole may be drilled through the non-porous section into the porous section into which is placed the driving means and active agent. Fluid may pass through the porous section and activate the swellable agent.

Alternatively the device comprises a non-porous polymer housing closed by a water impermeable adhesive plug. A molecular wick is grafted onto the inner surface of the non-porous shell to provide a passage for conveying external fluid to one or more expandable layers located within the device.

In a further embodiment of the invention the device comprises a cylindrical non-porous polymer housing open at one end and closed at the other end by a extruded polytetrafluoroethylene rope inserted into the cavity of the housing. The polytetrafluoroethylene fibre making up the rope has had its internal surface treated by graft polymerisation of an hydrophilic polymer onto the surface thereof. In use the polytetrafluoroethylene rope provides capillary passages to a swellable agent, for example, a hydrogel, located adjacent the inner end of the rope.

The invention also provides a method for administering an active material to a subject the method including delivering the active ingredient(s) using a device in accordance with the present invention.

The various arrangements and alternatives described in relation to the invention in its first embodiment may also be used where appropriate, in this embodiment.

The present invention also provides a method of dispensing an active agent using a device in accordance with the present invention.

DESCRIPTION OF EXAMPLES

Having broadly portrayed the nature of the present invention, the invention will now be described by way of illustration only. In the following description, reference will be made to the accompanying drawings in which:

FIGS. 1A and 1B demonstrate that the capillary passages of the porous polyethylene (PE) have been infiltrated with vascular endothelium (E) and connective tissue. Red blood cells (RBC) are evident in the blood vessels which demonstrate that body fluids are being imbibed to the swelling agent via the capillary passages within the device and that the PE is not acting as a semi-permeable membrane.

FIG. 5 is a longitudinal section of a passive multi-dose device having wick-fed to the sequential expander, which comprises the fourth example;

FIG. 6 is a two-stage passive multi-dose device which comprises the fifth example of the invention; FIG. 6A is a longitudinal section and FIG. 6B is an end elevation.

FIG. 7 is an end elevation and FIG. 7A is a partial longitudinal section of a device which comprises the sixth example.

Figure 10A:
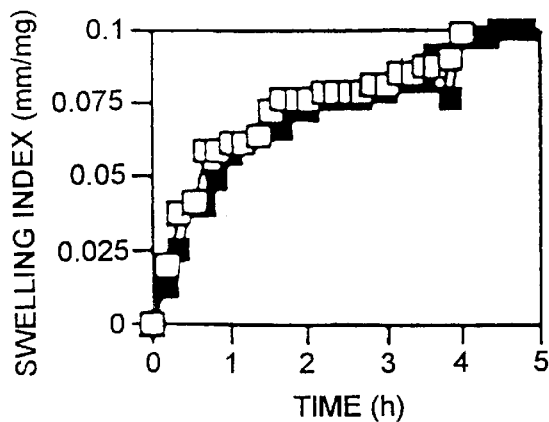
FIG. 10A is graph showing the swelling characteristics of hydrogel in a test device described in the eighth example.
Figure 10B:
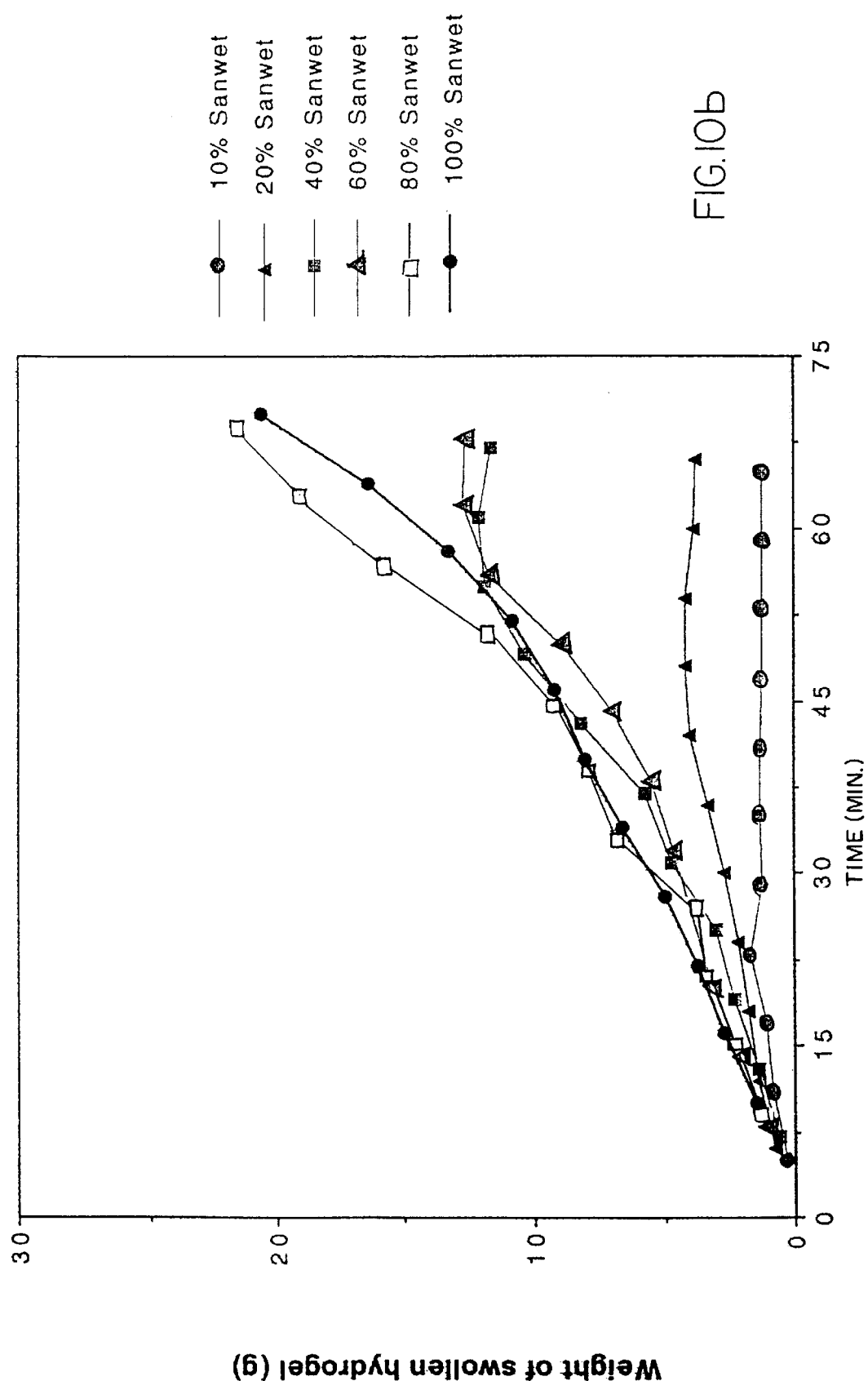

FIG. 10B shows that the swelling of the hydrogel in free solution is proportional to the amount of swelling agent within the driver. This experiment was conducted by allowing the driver (containing various amounts of SANDWET) to swell in an aqueous medium containing phosphate buffered saline. The swelling was estimated by measuring the increase in weight of the wet hydrogel collected on a sieve filter.

Figure 10C:
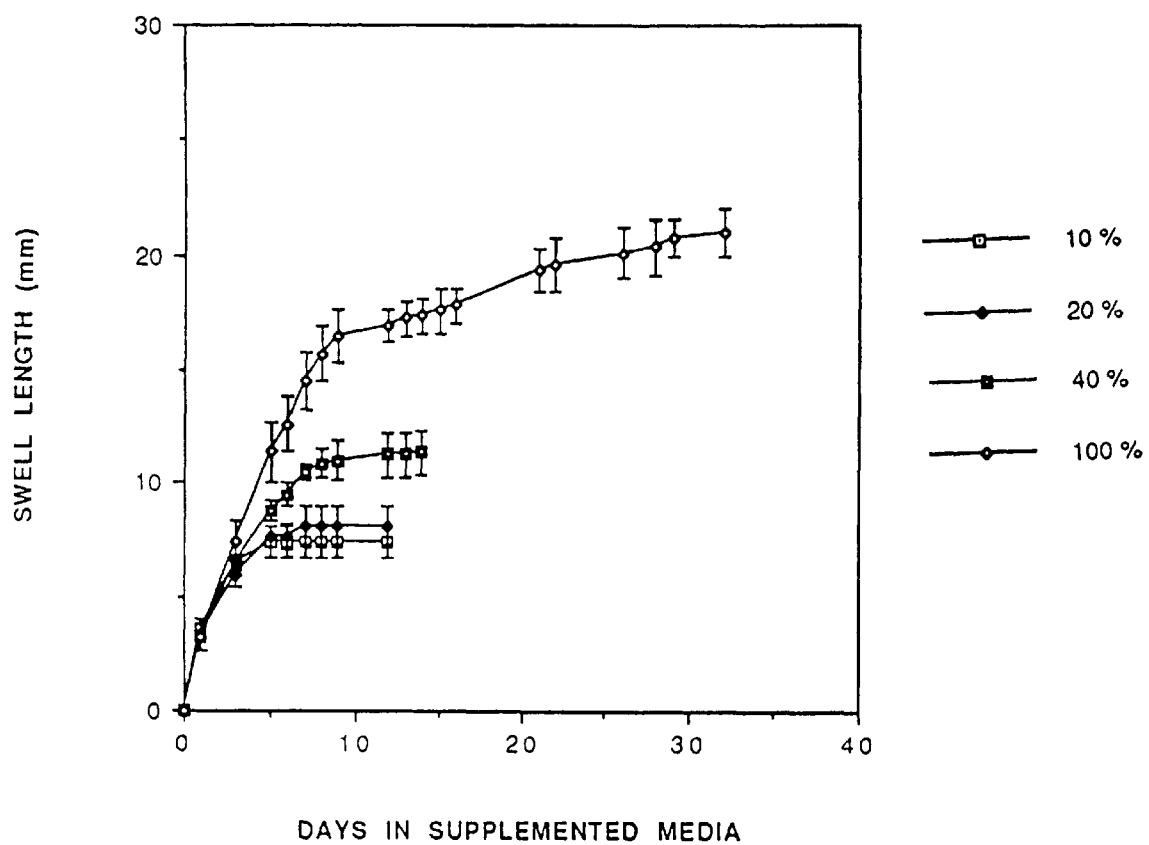

FIG. 10C shows that results of an experiment in which drivers containing varying amounts of SANDWET swelling agent (10–100%(w/w)) were used in transparent devices and the length of driver was measured for a minimum of 12 days. The results show that the swelling of the driver is biphasic and that the rates of swelling during both initial fast and delayed slow phases are proportional to the amount of Sandwet with the driver containing 100% (w/w) SANDWET having the fastest rates of well.

Figure 11:
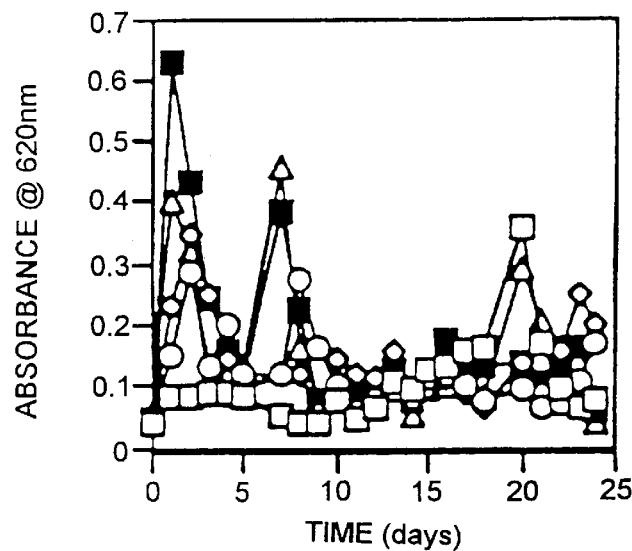

FIG. 11 is a graph showing the characteristics of release of bioactive from the test devices driven by hydrogel as described in the eighth example.

Figure 13B:
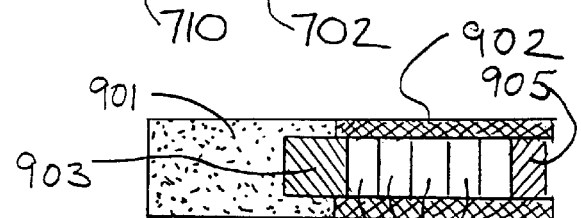
Figure 12:
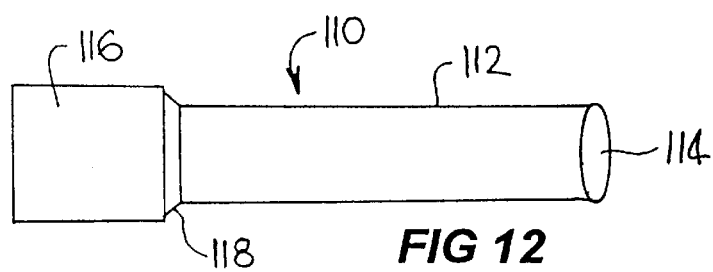
Figure 13A:
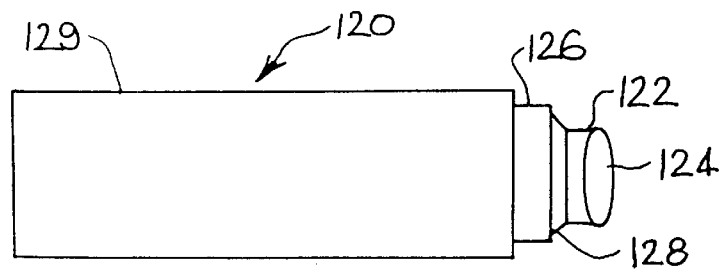

FIGS. 12 and 13A are schematic views of various further embodiments of the invention.

FIG. 13B shows an alternative arrangement wherein the housing is constructed from a rod that includes a porous section (901) at one end and a non-porous section (902) at the other. The material that the rod is made out of is UHMW polyethylene and it is constructed from two smaller rods, one porous and the other non-porous, held together in a die under pressure and heated. A hole is then drilled through the non-porous section into the porous section into which is placed the swellable agent (903), layers of active agent (904) and plug (905). The rod can also be constructed out of PTFE, HDPE, PEEK, Polyimide and other, including biodegradable, polymers.

Figure 14A:
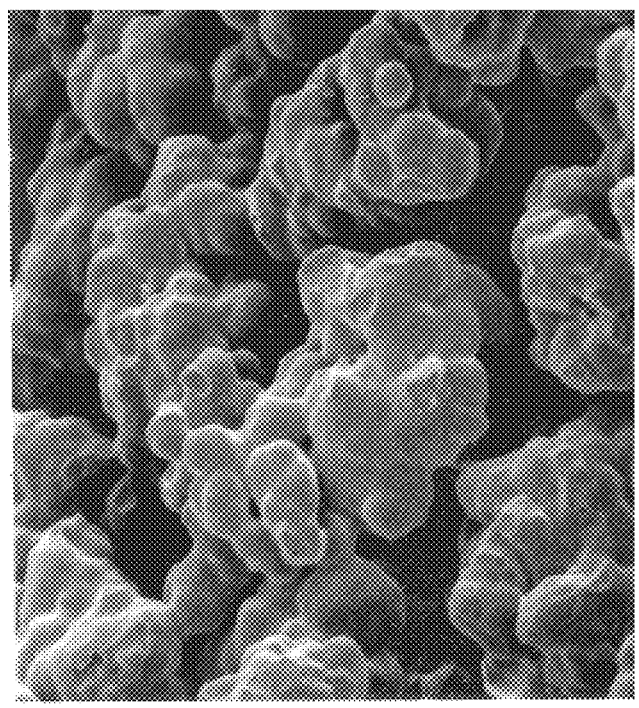

FIGS. 14A and B show scanning electron micrographs of a porous and non-porous polymer.

Figure 15:
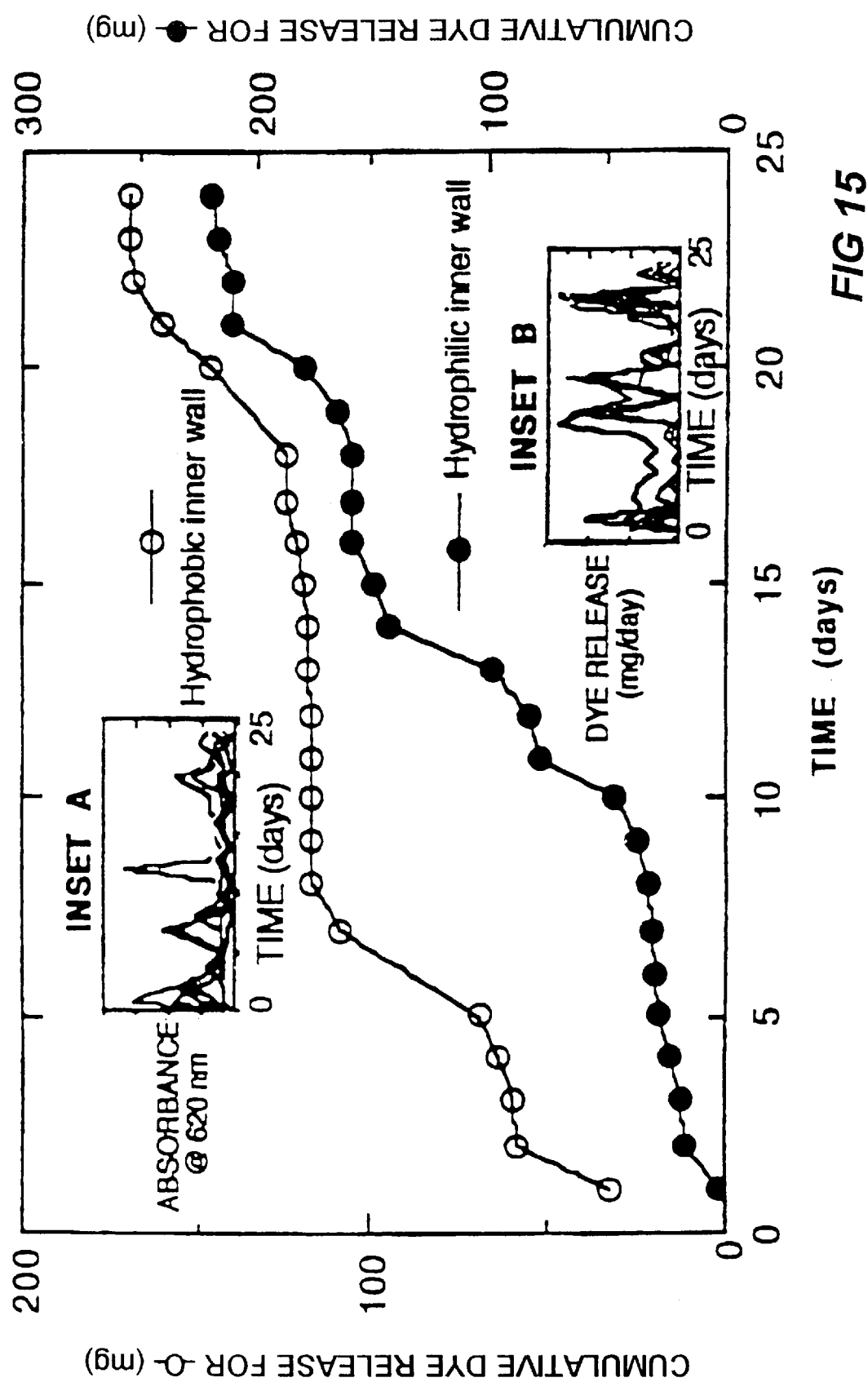

FIG. 15 is a graph showing the effect of changing the hydrophilic/hydrophobic nature of the inner wall of the device described in Example 8 on pulsatile release.

Figure 16:
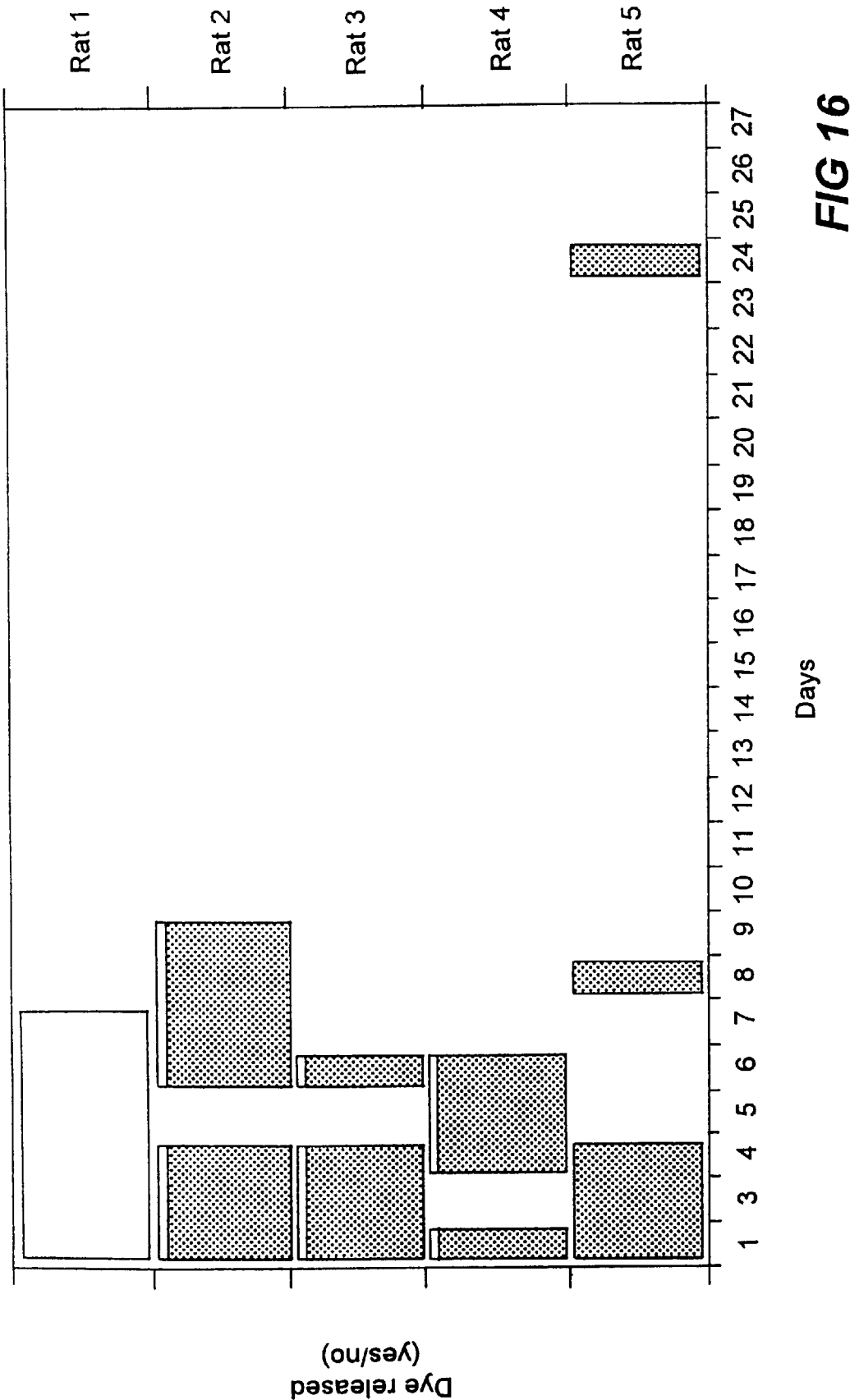
Figure 18A:
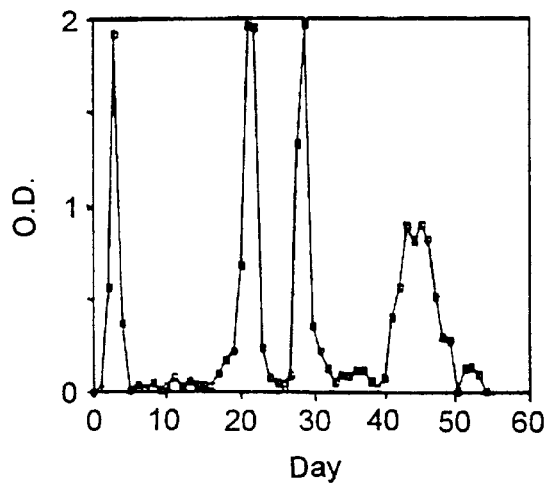
Figure 18B:
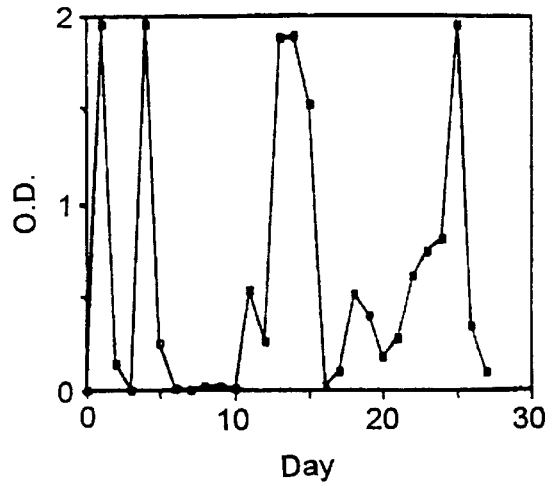
Figure 18C:
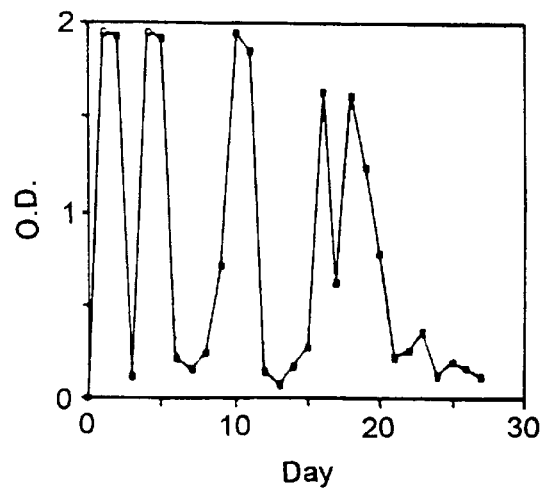
Figure 18D:
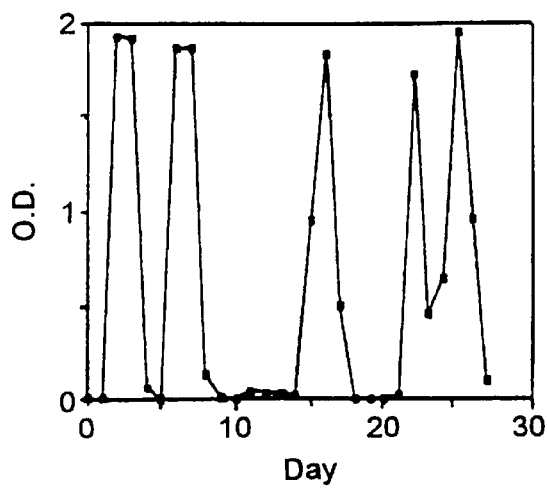

FIG. 16 shows the pulsatile release of a bioactive marker from the device described in Example 8 in male PVG/C inbred rats.

FIG. 17 is a longitudinal section of a multi-stage capsule formed from biocompatible materials. FIG. 17A is a modification of the embodiment illustrated in FIG. 17 utilising a porous inner plug.

Figure 20:
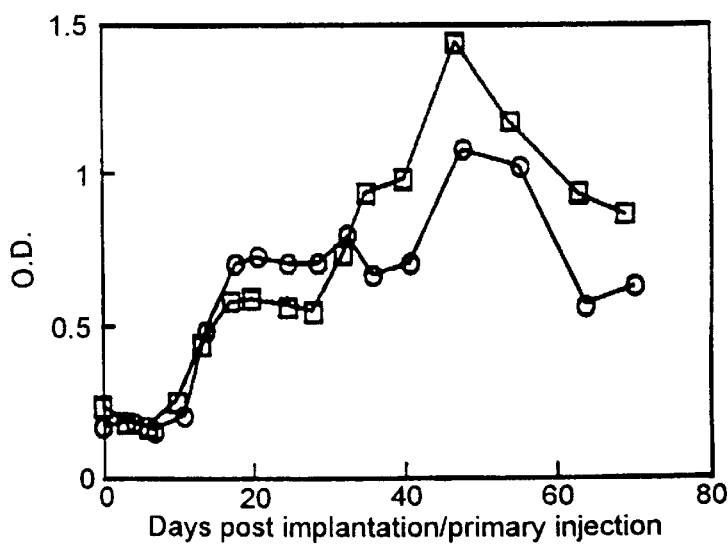

FIGS. 18A to D are a series of in vitro release profiles for the device of FIG. 20.

Figure 19A:
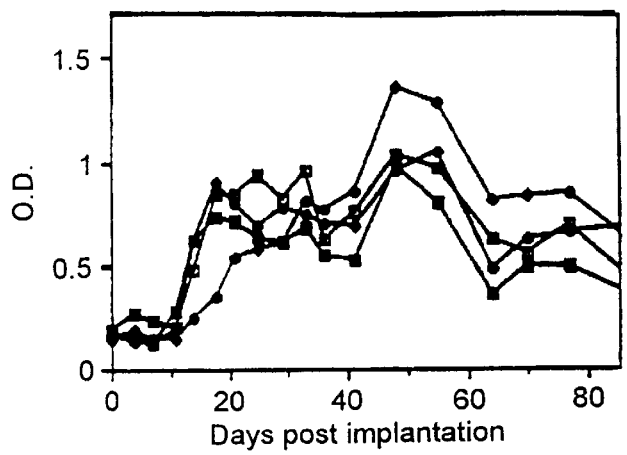

FIGS. 19A and B illustrate individual anti-tetanus antibody responses of sheep implanted with a pulsatable antigen delivery device.

FIG. 20 compares the mean responses shown in FIGS. 19A and B.

Figure 21:
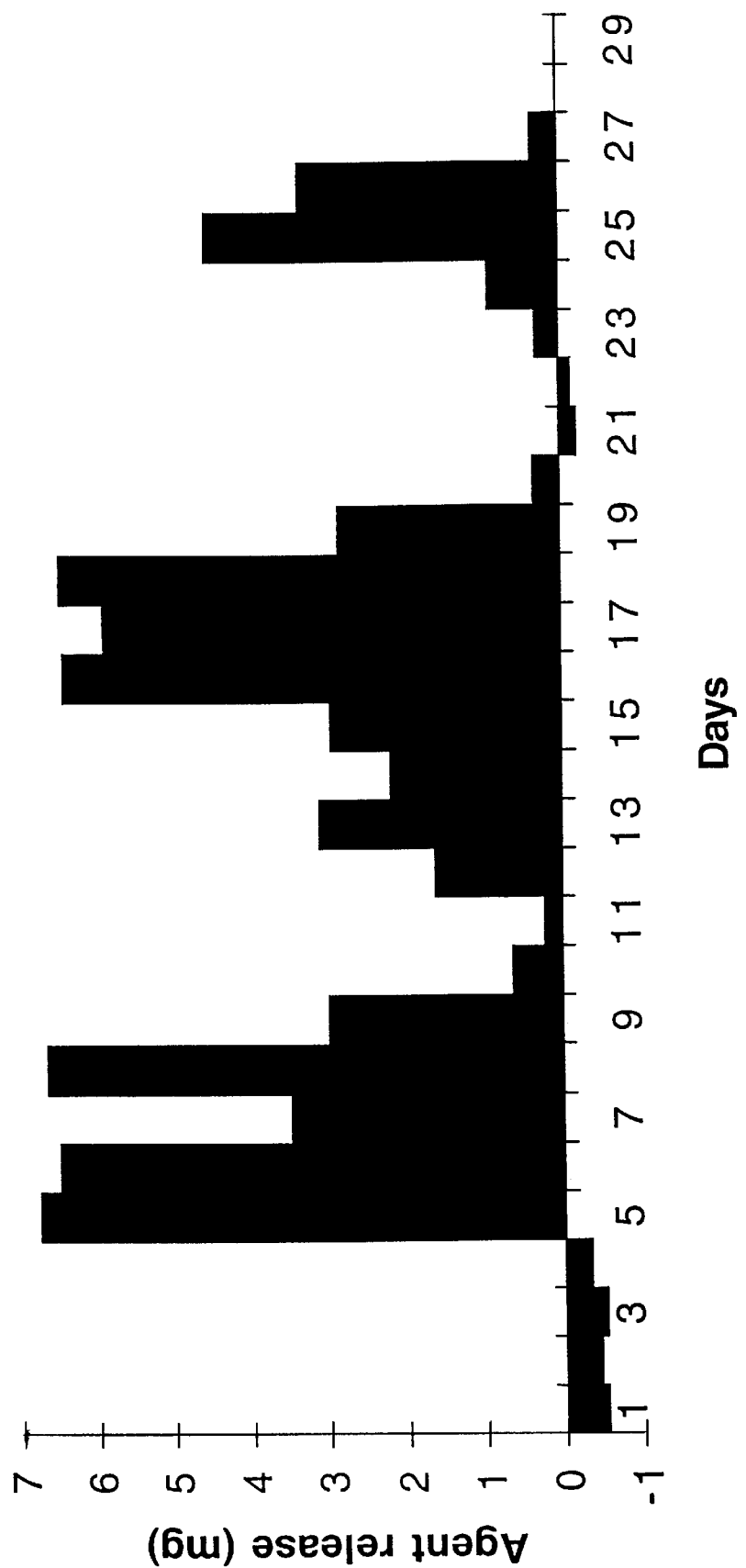
Figure 22:
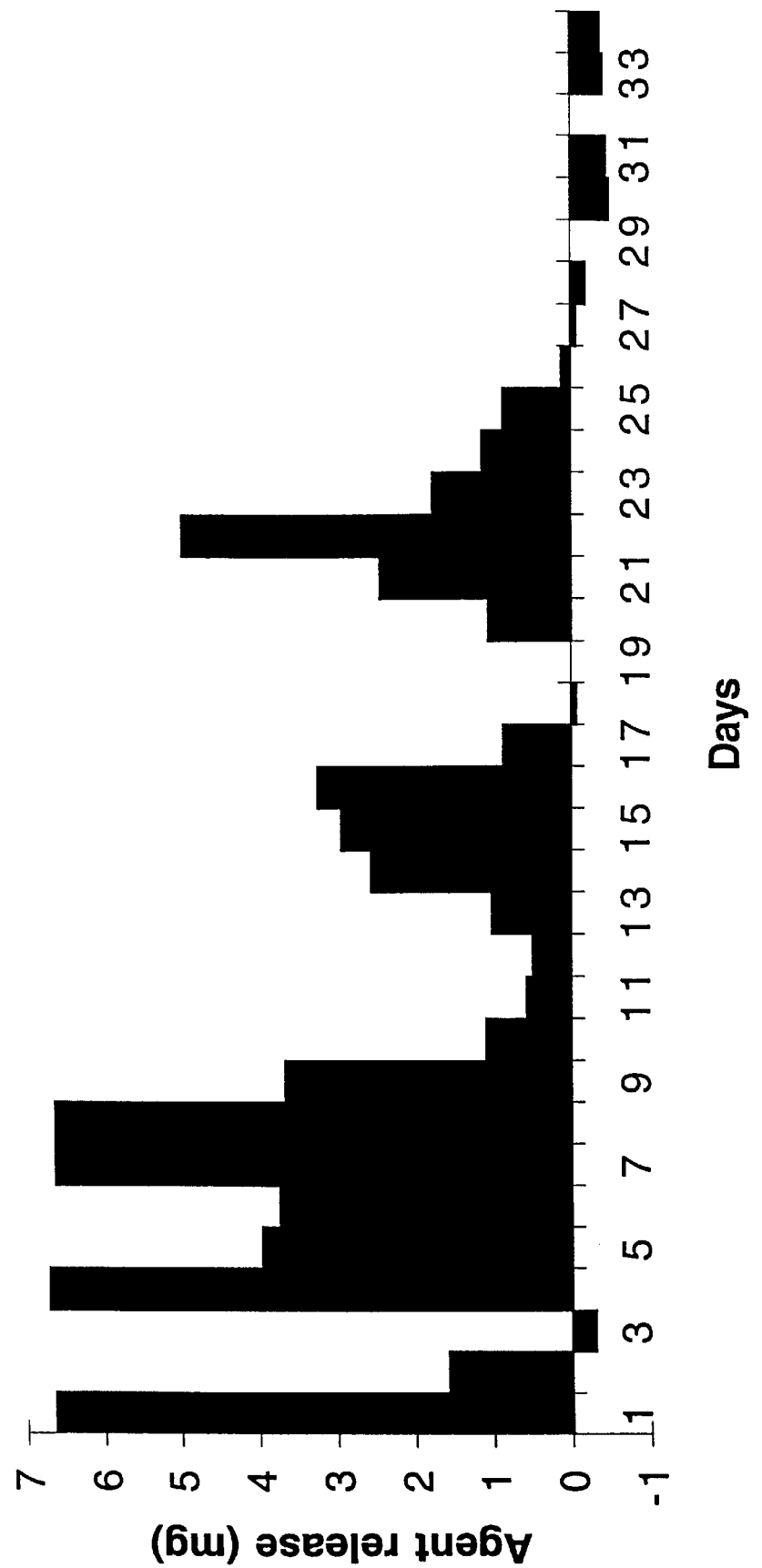

FIGS. 21 and 22 show the effect of varying the polymer type (PE versus PVDF) of the porous capillary passages on the release profiles of devices which have the capillary passages at the base of the device as shown in FIG. 17A. FIG. 21: prototype device using PE wick, lactose spacers and castor oil lubricant; FIG. 22: prototype device using PVDF wick, lactose spacers and castor oil lubricant. The device completely expels the layers by 23 to 25 days when a more hydrophilic polymer PVDF is used compared to 25 to 28 days when PE is used.

Figure 23A:
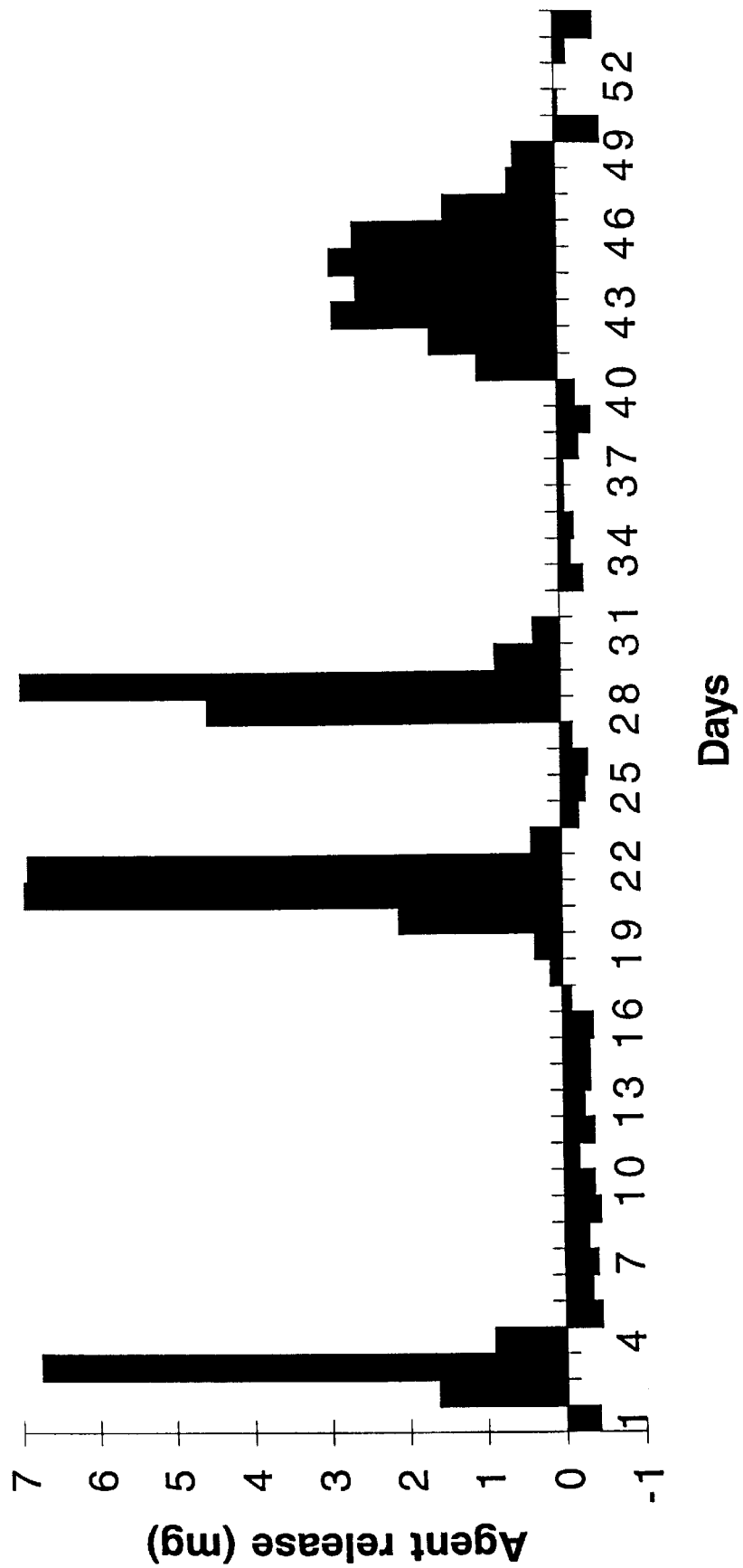
Figure 23B:
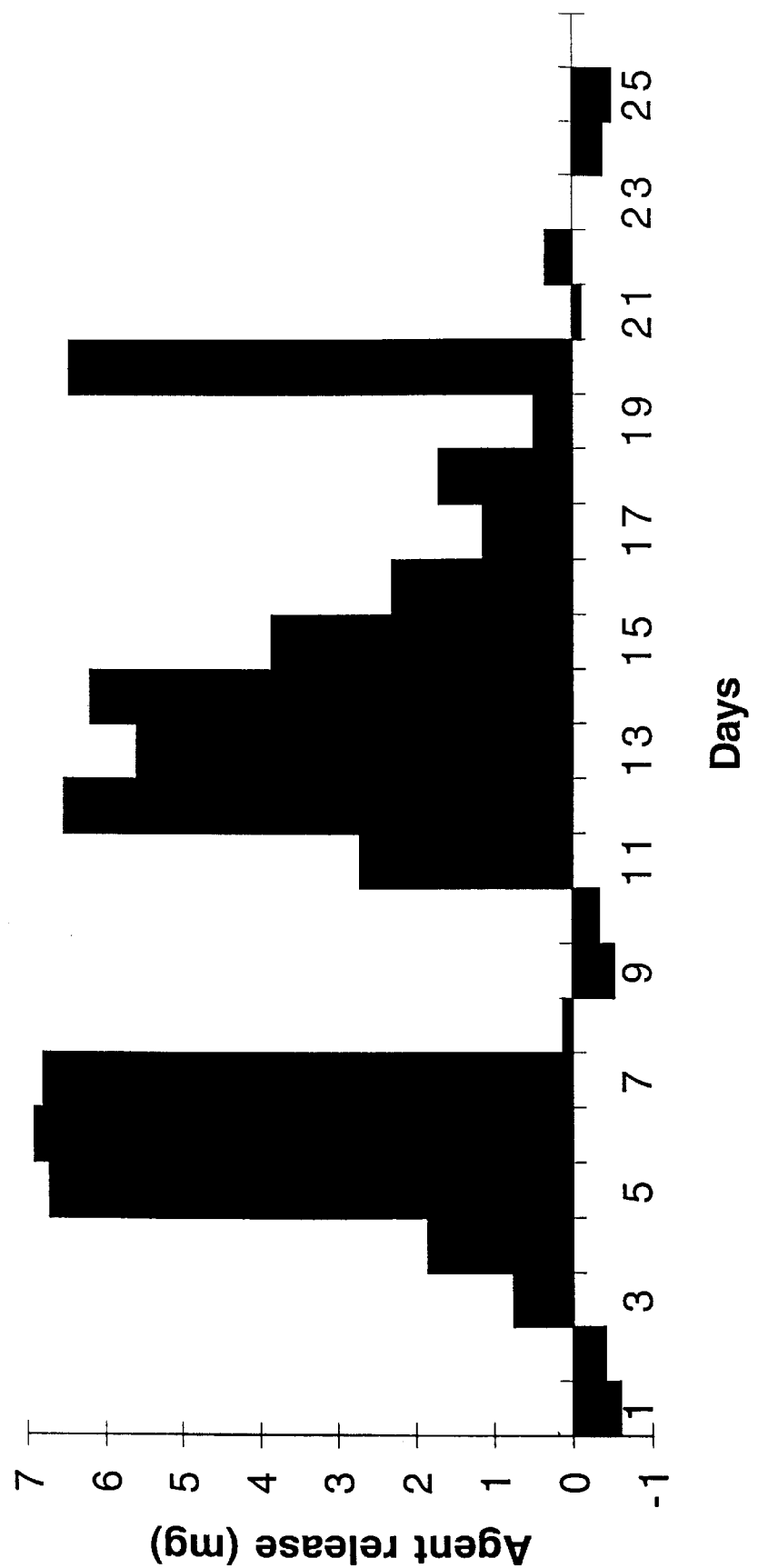

FIG. 23 shows the effect of varying the spacer excipient formulations (polyethylene glycol versus glycerol monostearate) on the release profile of devices which have the capillary passages at the base of the device as shown in FIG. 17A. FIG. 23A: prototype device using PE wick, glycerol monosterate, spacers and castor oil lubricant; FIG. 23B: prototype device using PE wick, 1% PEG spacers and castor oil lubricant. When PEG is used as an expanding, hydrophilic spacer, the delay between the active layers was decreased (FIG. 23B) when compared to using a hydrophobic and non-expanding glycerol monostearate based spacer (FIG. 23A).

Figure 24A:
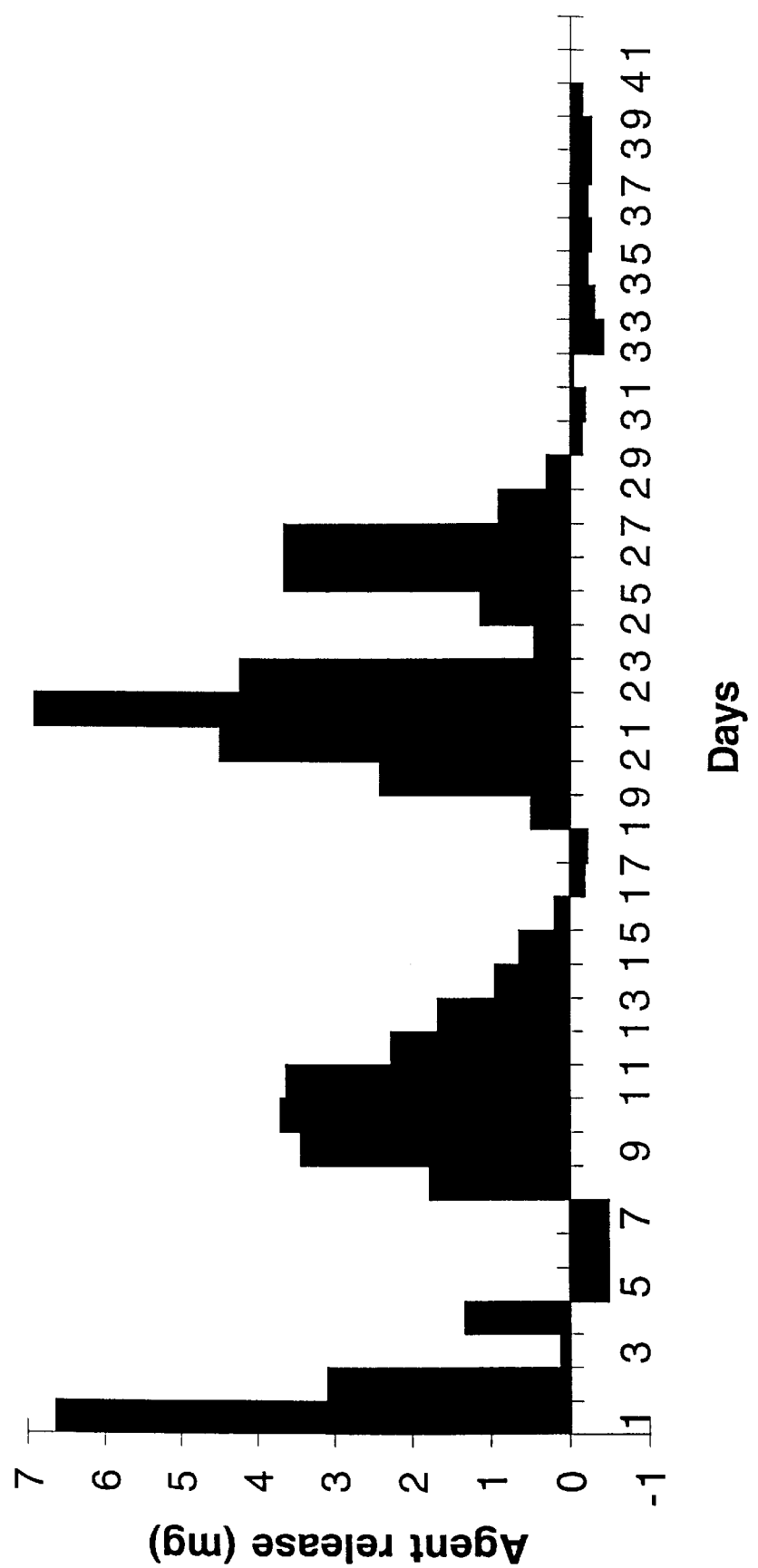
Figure 24B:
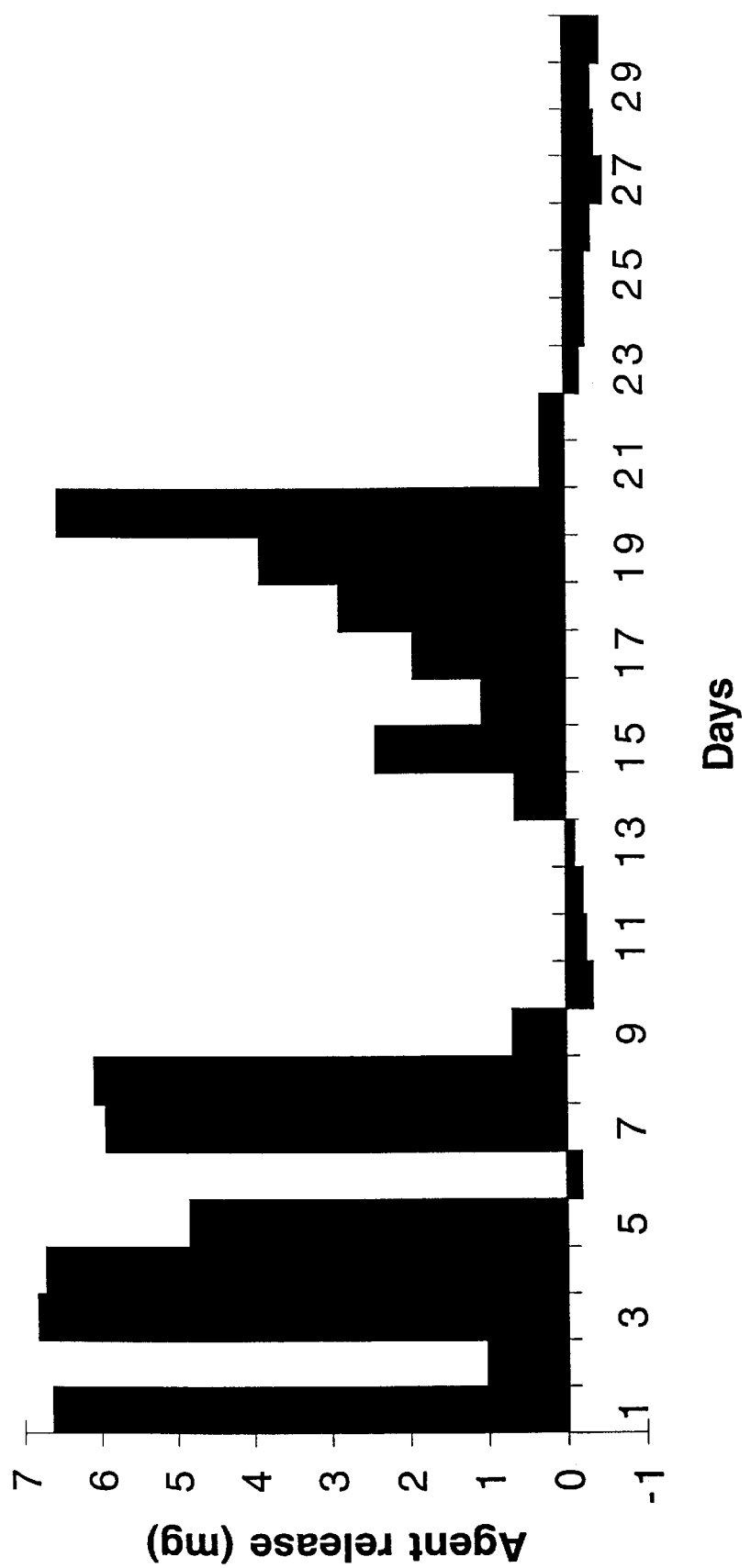

FIG. 24 shows the effect of varying the lubricant on the release profile of the devices (castor oil, vasoline and none). FIG. 24A: prototype device using PE wick, lactose spacers and no lubricant; FIG. 24B: prototype device using PE wick, lactose spacers and vaselike lubricant.

Figure 25A:
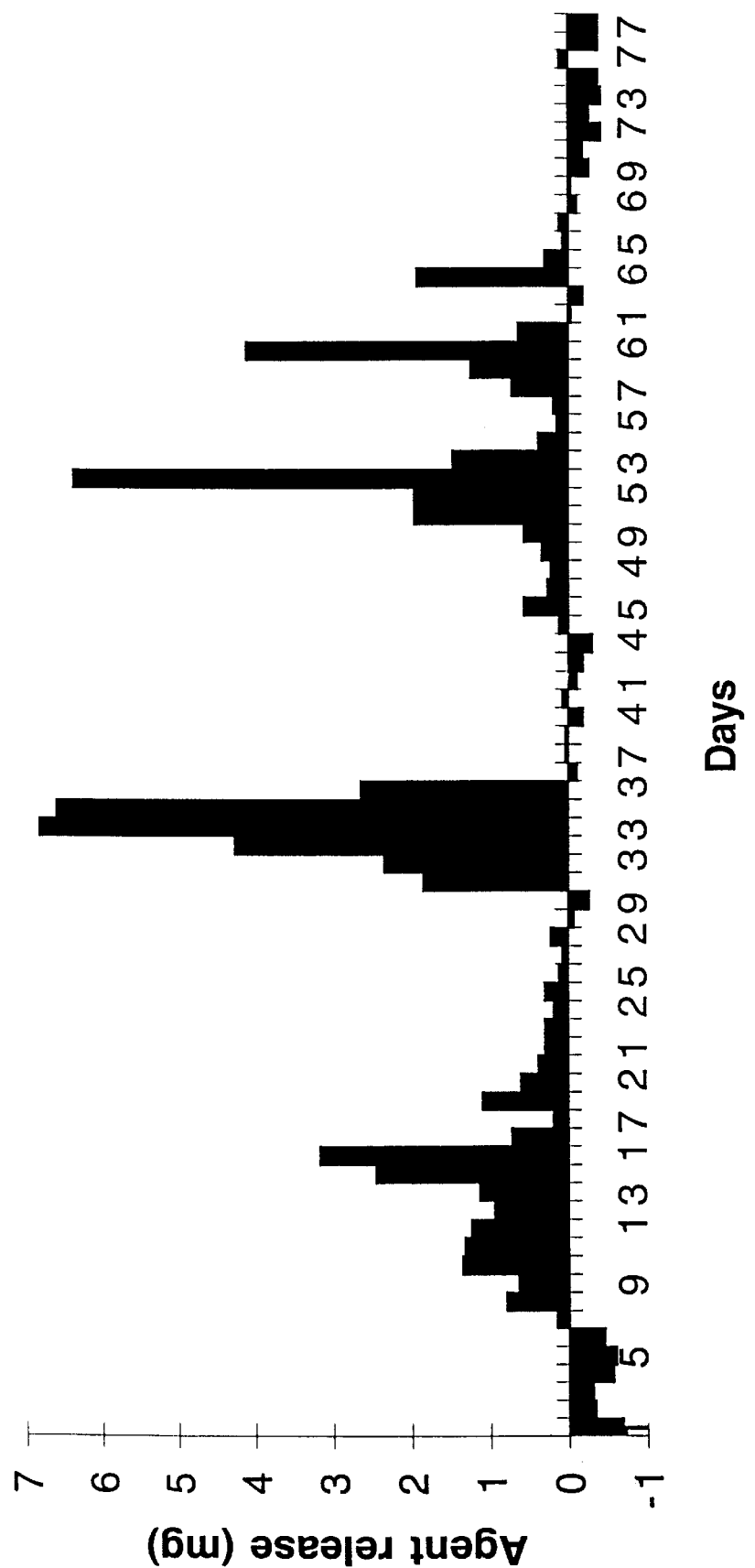
Figure 25B:
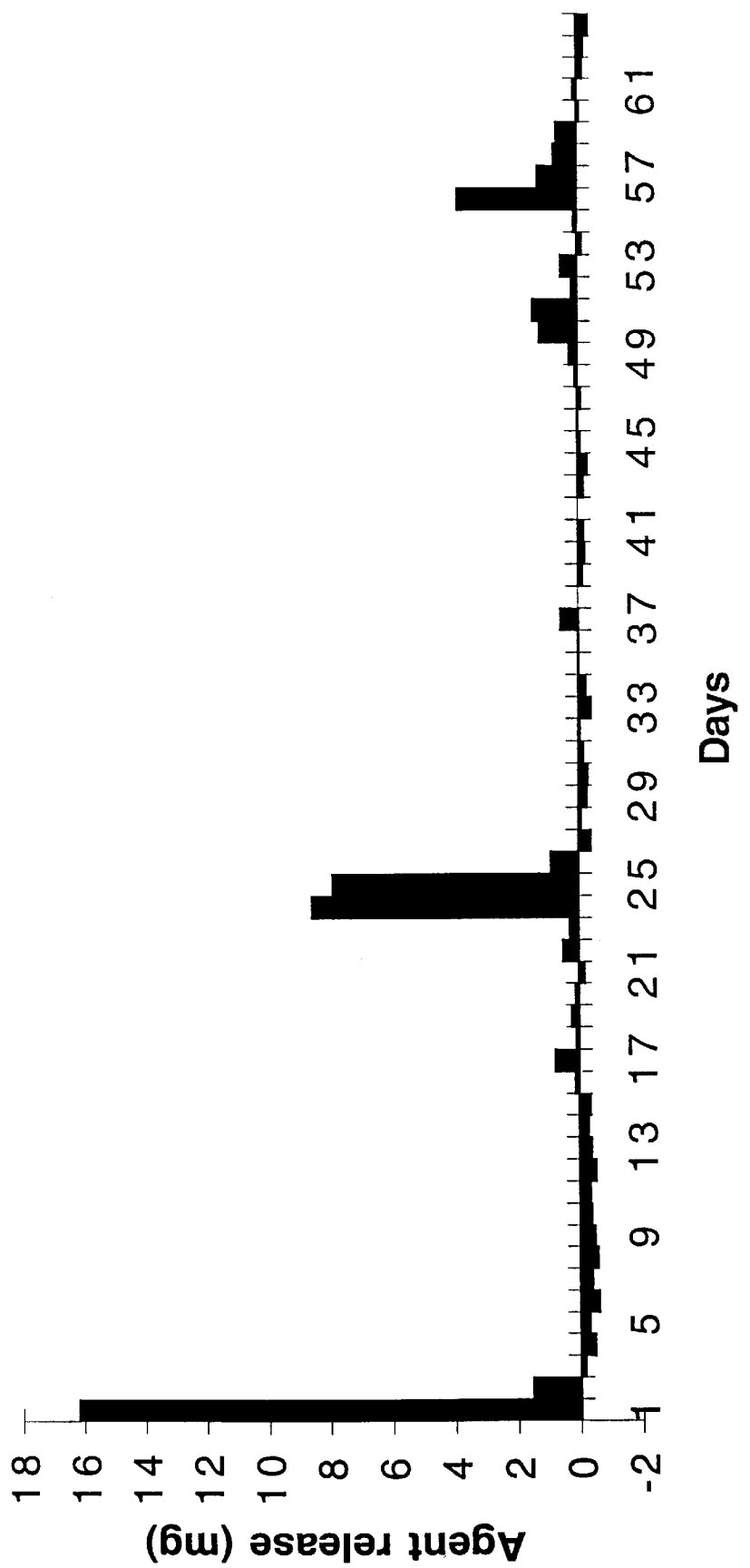

FIG. 25 shows the effect of varying the polymer type of the impervious housing on the release profile of the devices (FEP versus Polystyrene). FIG. 25A: prototype device using PE wick, and housing as in FIG. 13, lactose spacers and caster oil lubricant; FIG. 25B: prototype device using PE wick and housing as in FIG. 13, glycerol monostearate spacers and caster oil lubricant.

Figure 26A:
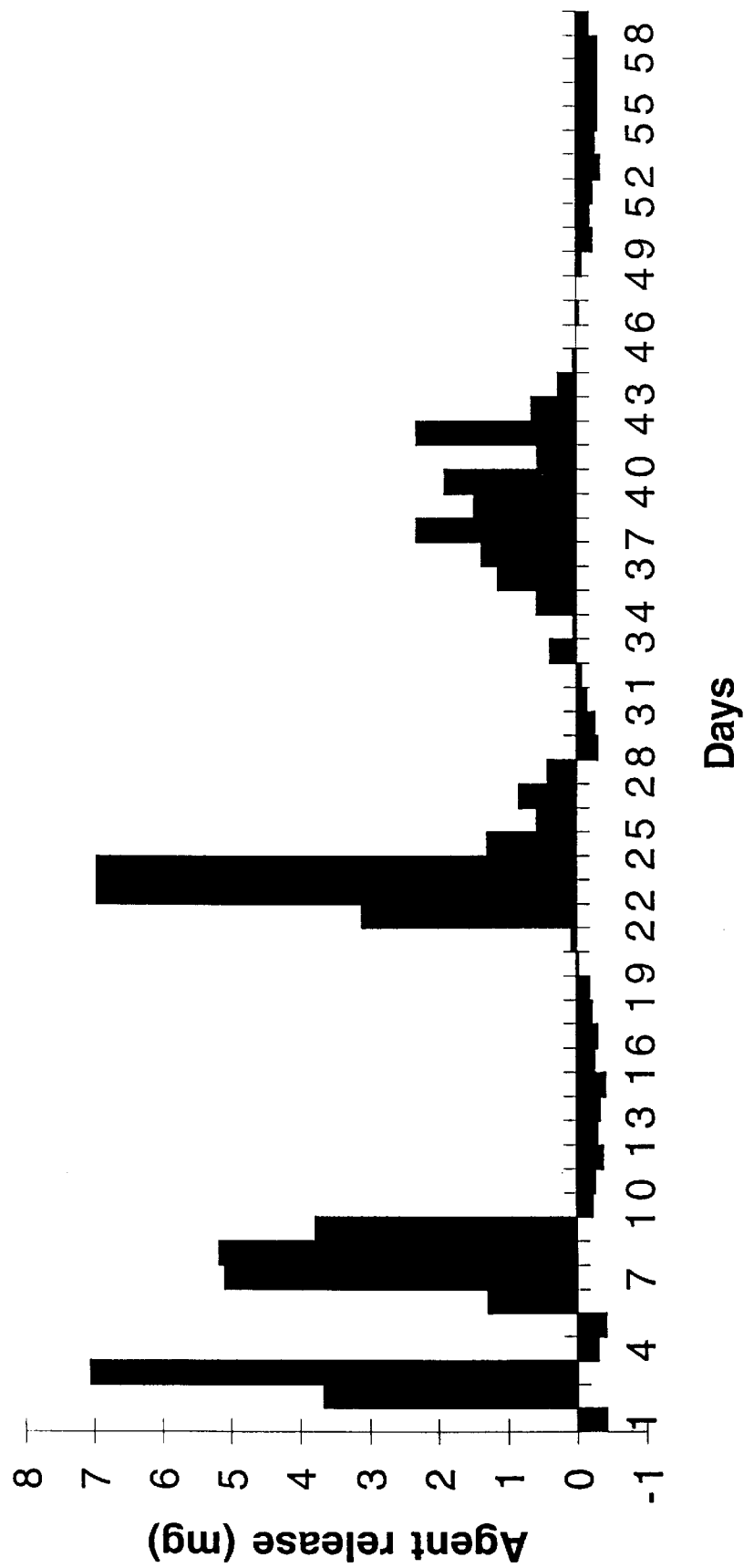
Figure 26B:
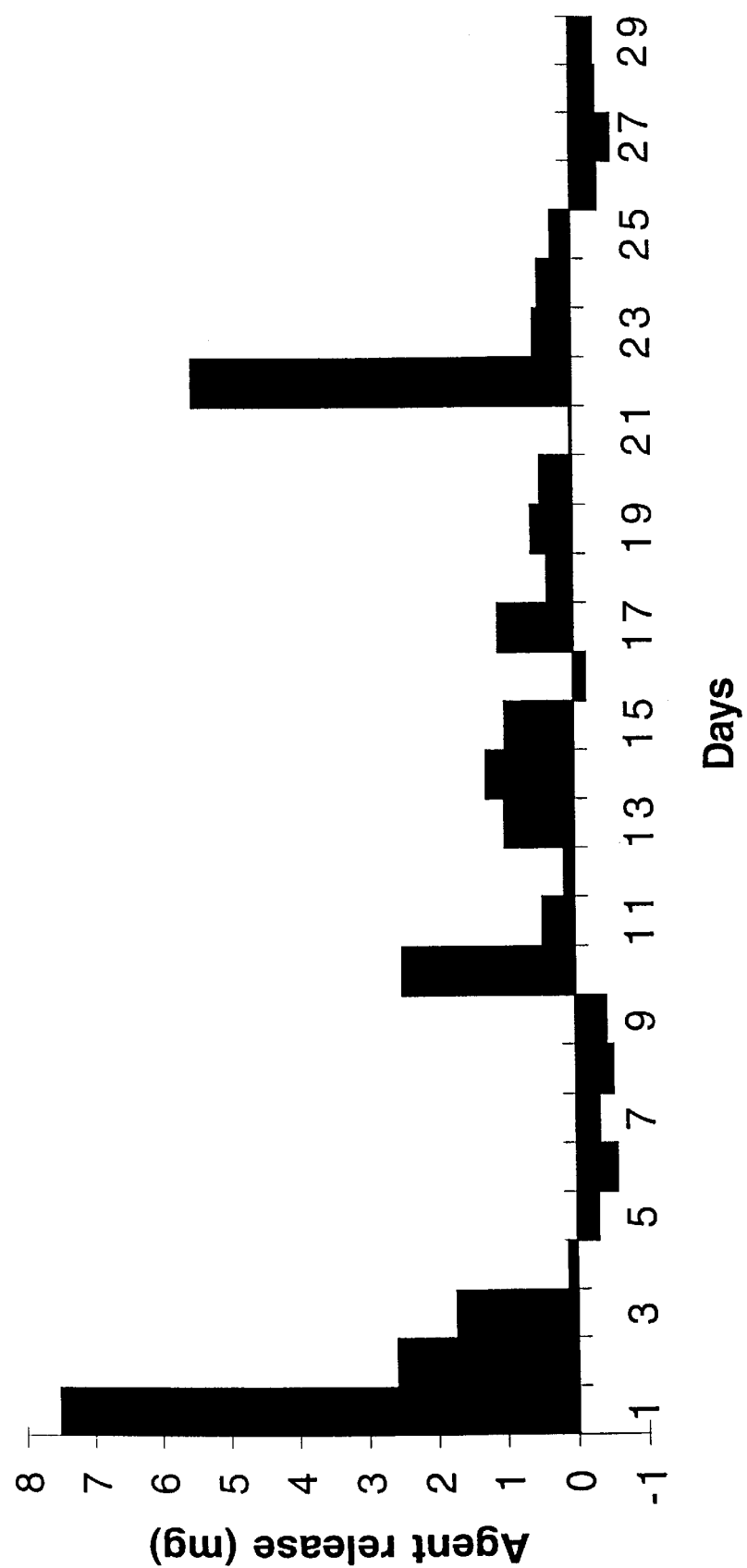

FIG. 26 shows the effect of using hydrophilic (lactose) and hydrophobic (glycerol monostearate) excipient formulations as spacers on the release profile of devices which have the capillary passages running along the length of the device as shown in FIG. 13. FIG. 26A: prototype device using PE wick chemically adhered to the inside of a polystyrene housing (FIG. 17B), glycerol monostearate spacers and caster oil lubricant; FIG. 26B: prototype device using PE wick inside heatshrunk FEP housing (eliminating use of adhesive, FIG. 17B), glycerol monostearate spacers and caster oil lubricant.

Figure 27:
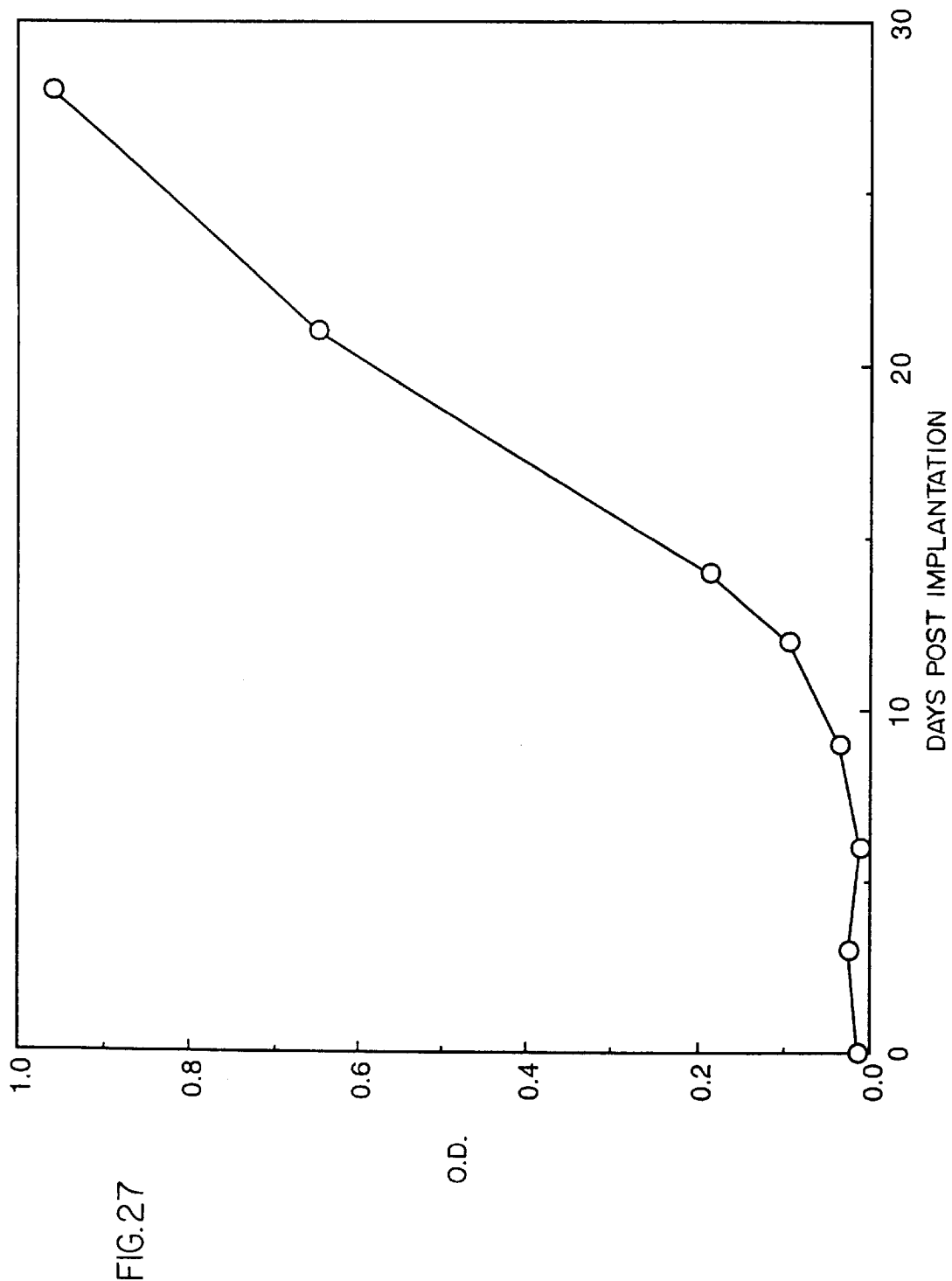

FIG. 27 shows the temporal antibody response to the in vivo release of a model antigen (tetanus toxoid) in rats. The experimental rats were implanted with prototype device using PE wick and FEP housing as in FIG. 17B, glycerol monostearate spacers and castor oil lubricant.

Figure 28A:
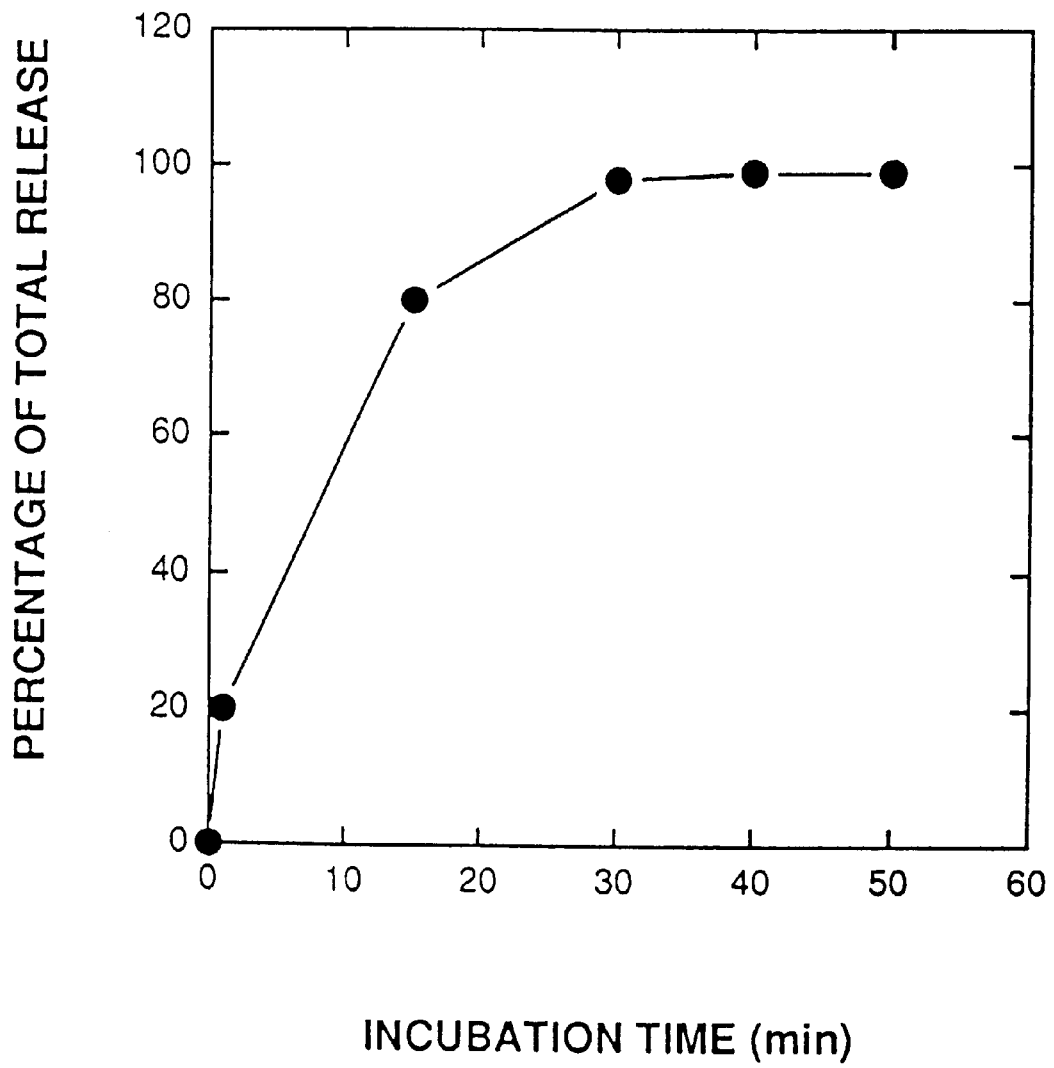

FIG. 28A shows the in vitro dissolution release profile of active (in this case a model antigen, tetanus toxoid) from a tablet formulated with the lactose, cellulose and magnesium stearate excipients. The results show that most of the active is released from the formulated tablet (i.e. the said active layer component of the device). Tablets containing approximately 100 $\mu$g of toxoid were prepared. The rate of release or protein from within the tablets was determined by measuring the residual protein that was released in Dulbecco's Modified Eagle Media (DMEM. Gibco-BRL, New York, United States of America) supplemented with 10% (v/v/) foetal calf serum, 2 mM glutamine, 100 U/mL penicillin and 0.1 mg/ml streptomycin (FCS, CSL Ltd., Melbourne, Australia), at 15 minute intervals until the tablet was fully dissolved. Particulate matter was then removed by centrifugation at 14,000×g. The protein concentration of the supernatant was analysed using the BCA protein assay technique. Results were expressed as a percentage of the total tetanus toxoid protein compressed within the tablet.

Figure 28B:
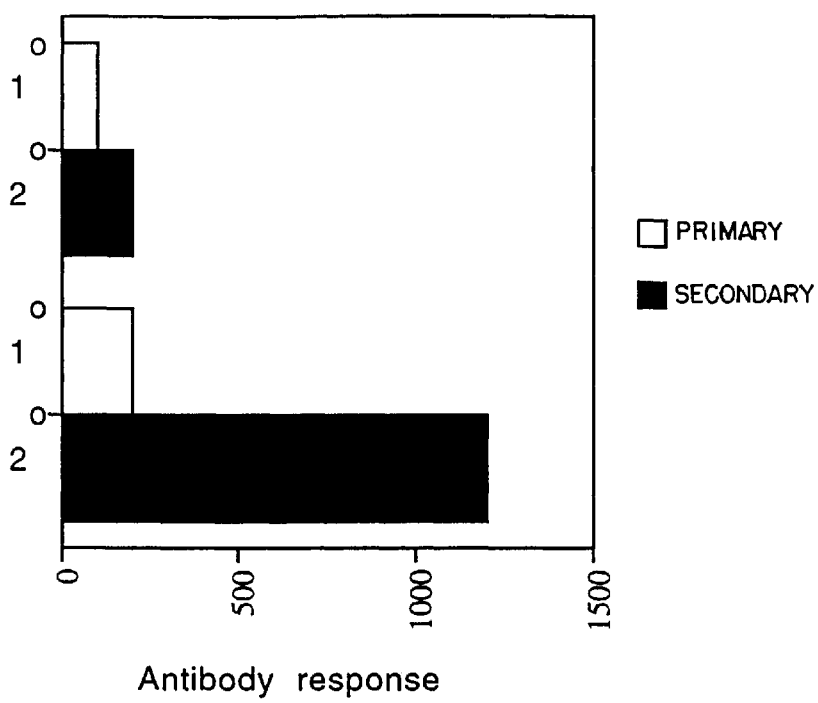
Figure 28C:
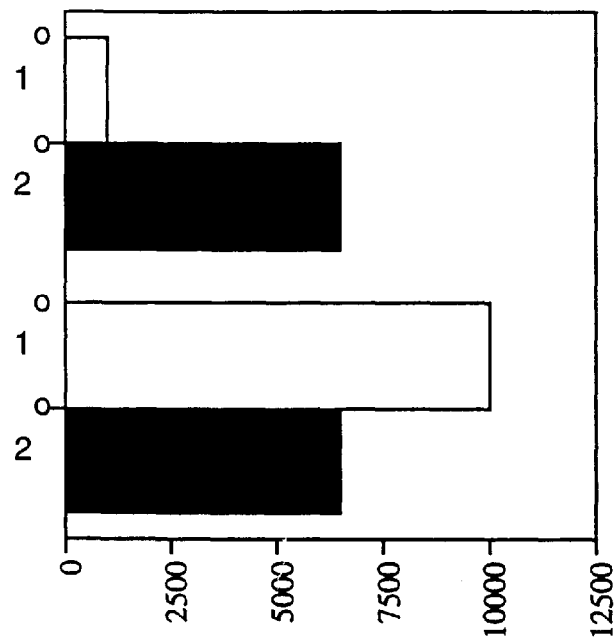

FIGS. 28B and 28C shows the in vivo primary and secondary antibody responses of mice immunised with model antigens administered as a table formulation or as a liquid adjuvanted formulation. Groups of mice received 2 identical subcutaneous immunisations delivered 4 weeks apart of either KLH (FIG. 28B) or tetanus toxoid (FIG. 28C). The total dose of antigen was 5 $\mu$g in either a solid formulation containing the lactose, cellulose, magnesium stearate mix or as a liquid formulation containing 100 $\mu$l of 0–6 mg/ml aluminium hydroxide gel in 50 mM phosphate buffered saline and/or 0–100 $\mu$g IL-1. Antibody responses were measured 19 days post the initial primary and secondary immunisations. The results show in both cases, that the proposed tablet formulation generated far improved immune responses compared to responses when the antigens were administered in liquid adjuvanted form.

EXAMPLE 1

Figure 1A:
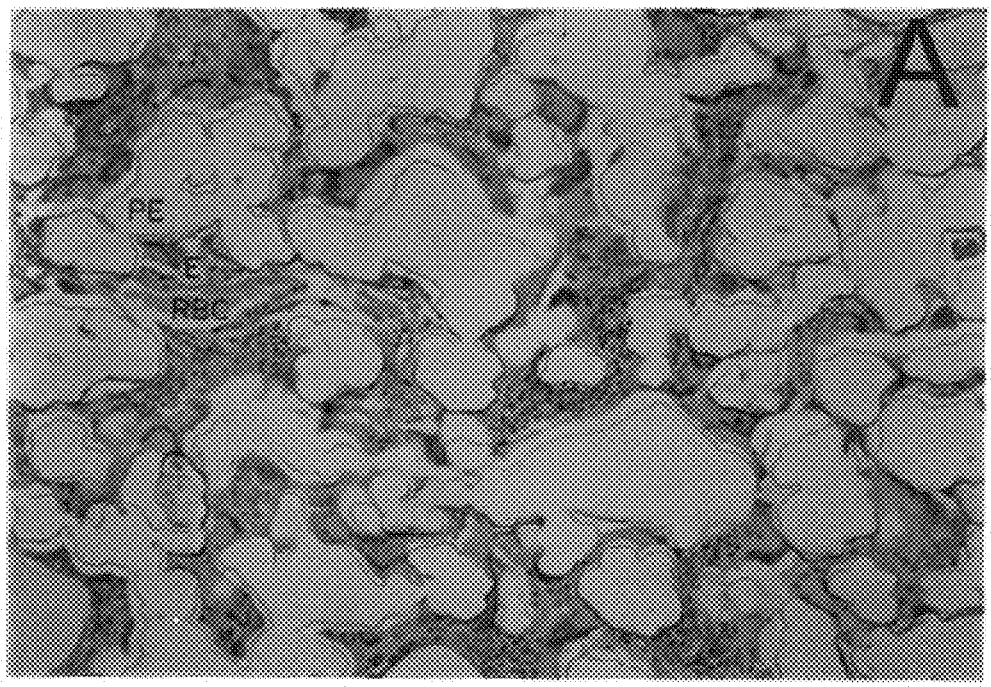
Figure 1B:
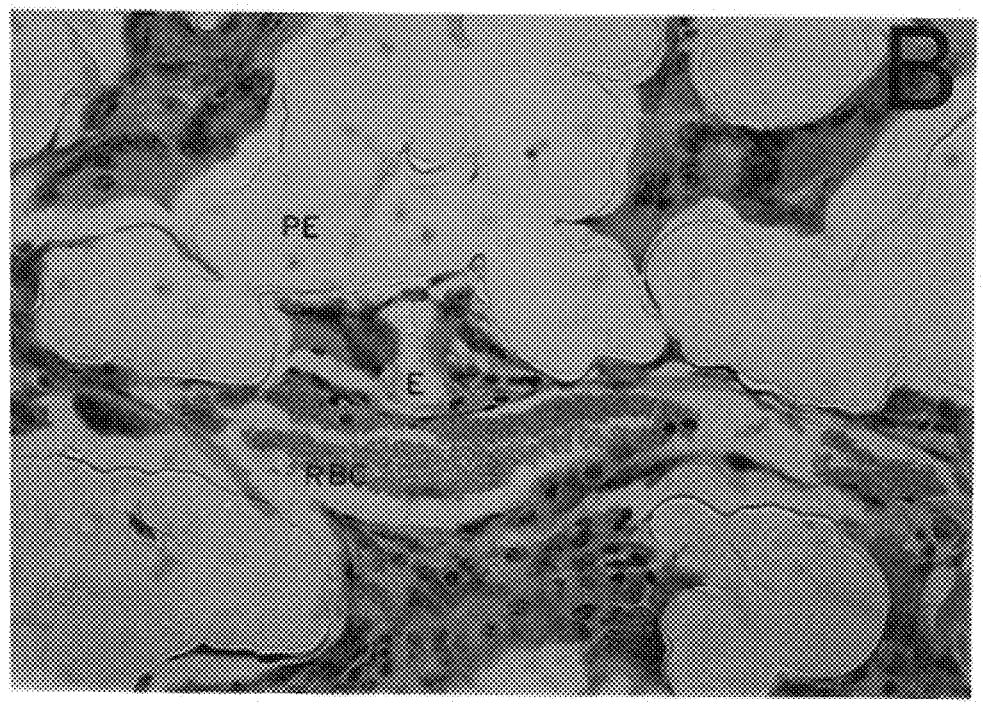
Figure 2:
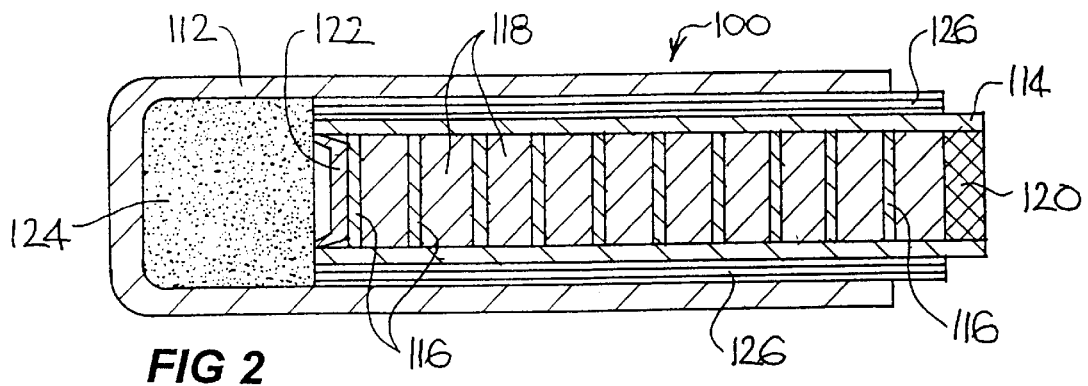
FIG. 2 is a longitudinal cross-section of an active multi-dose device with a wick-fed hydrogel swellable agent, which comprises the first example.

Referring to FIG. 1, the first example of this invention comprises an active dose multi-dose capsule 100 having a non-porous, e.g. heat-shrink, outer casing 112 and a non-porous polyethylene and for polystyrene liner tube 114 containing a stack of alternative active and passive layers (116 and 118 respectively). The outer end of liner 114 is closed with a protective plug 120, while the inner end is closed by a biocompatible plastic piston 122. A dry hydrogel expandable element 124 is located between closed end of casing 112 and the inner end of liner 114 and piston 122. Between 112 and 114 a layer of porous polyethylene 126 about 0.60 mm thick forms a wick that is adapted to convey water from outside the capsule to swellable element 124.

In this example, the swellable element was a tablet of 0 to 100% (w/w) SANDWET* in an excipient base comprising 0 to 95% (w/w) lactose, 0 to 40% (w/w) cellulose and 0 to 20% (w/w) magnesium stearate. For experimental purposes, both the active and the passive layers (116 and 118) were formulated from the excipient base just described, except that the active layers additionally contained 1% a bioactive marker dye. In all, 20 active and 20 passive layers were incorporated into a test capsule of about 50 mm in length and 10 mm in diameter.

To test this capsule in vitro, it was immersed in 10 mL physiological saline and incubated at 37° C. for 24 days. Aliquots of the saline were removed each day for 24 days and examined in a spectrophotometer at 620 nm to determine the concentration of the marker in each aliquot. The saline was replaced daily to maintain the same volume throughout the test. After an initial delay of three days, regular peaks of the dye were observed over a period of approximately 25 days. By adjustment of the geometry of the capsule and its elements, it was found possible to obtain reliable 24 hour releases of dye over a period of 22 days from a capsule of 35 mm in length and 7.5 mm in diameter (FIG. 11). Such a capsule could therefore be applied to the delivery of porcine growth hormone.

EXAMPLE 2

The capsule 200 of the second example is of generally similar construction to that of the first example, having an impervious, biocompatible polymeric casing 212, a liner 214 containing a stack of alternating active and passive layers (216 and 218 respectively), optionally a driving piston 222, a swellable agent 224 and a wick 226 formed (as before) as an attached coating on liner 214. In this case, the driving mechanism is a swellable agent that swells on contact with water and consequently attracts water from the body fluids to permeate through the porous polymer along the wick to the agent which in turn creates a positive feedback effect. An important difference between the device of this example and that of Example 1 is that casing 212 extends beyond the ends of liner 214 and wick 226 so as to shield them somewhat from the environmental fluids.

Figure 3:
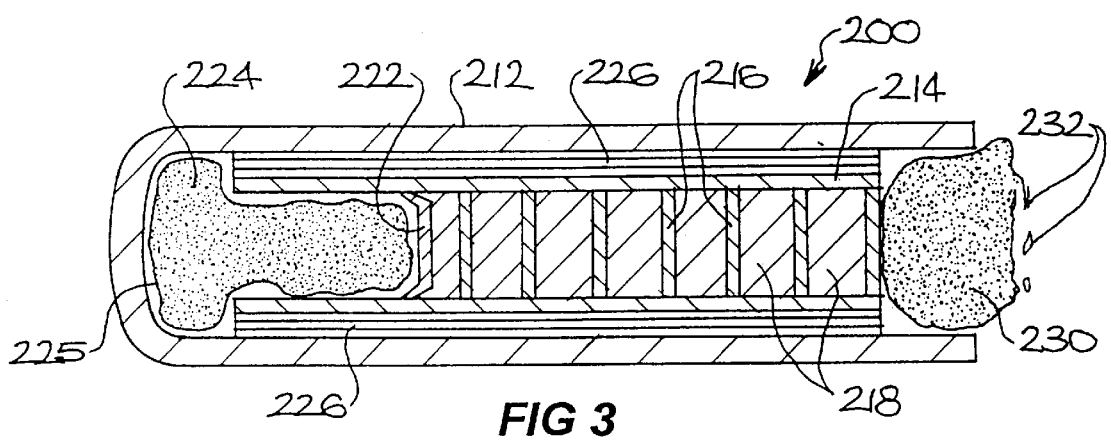
FIG. 3 is a longitudinal section of an active multi-dose device with a wick-fed osmotic swellable agent employing negative feedback, which comprises the second example.

Capsule 200 is illustrated in FIG. 3 as it might appear some time after implantation (or immersion in a test solution), swellable agent element 224 having been partially distended to move piston 222 partially along liner 214 to drive out the end plug (not shown) and a number of outer layers of the stack. The partially dissolved debris 230 of the last passive layer to have been ejected from liner 214 is shown at the mouth of capsule 200 with the last remnants 232 of the previous active layer. It will be seen that the remnants 230 and 232 will substantially change the composition of the fluid within the mouth of the capsule, reducing the concentration of water therein. This will, in turn, significantly reduce the flow of water along wick 226 to swellable agent element 224 with the result that expansion of element 224 will slow down until the debris 230 and 232 have been completely dissolved and dissipated within the body fluids.

Figure 19B:
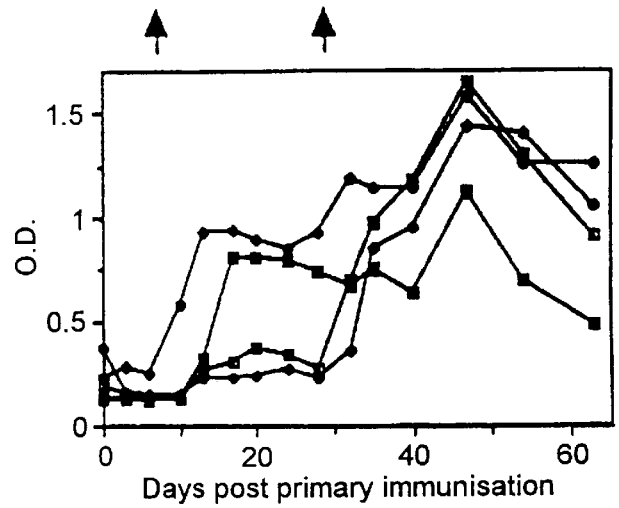

It has been found that capsules of this type can provide the dose-delivery profile of those of Example 1 while being substantially smaller. This again suits the delivery of porcine growth hormones, where the volume of hormone per dose is small, as well as vaccines. The data demonstrating this for vaccines is shown in FIGS. 18 to 20.

EXAMPLE 3

Figure 4:
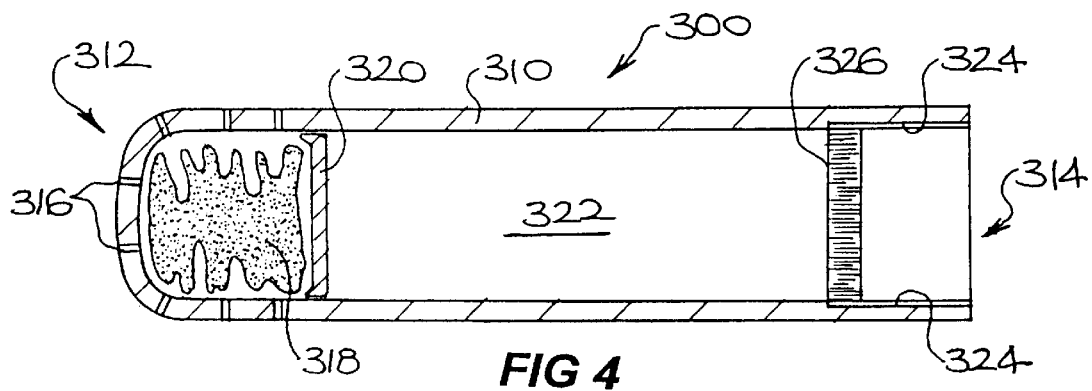
FIG. 4 is a longitudinal section of another multi-dose device (shown empty) with an osmotic swellable agent and a wick-driven layer expander, which comprises the third example.

The capsule 300 of the third example is shown in FIG. 4 and simply comprises an injection-moulded cylindrical casing 310 having a closed end 312 and an open end 314. Closed end 312 is perforated with a number of small diameter holes 316 which provide fluid access to the swellable agent element 318 which drives piston 320 along the bore 322 of the casing 310. FIG. 4 shows the capsule without its stack of layers.

At the open end, or mouth, 314 of casing 310, a pair of thin axially-extending wick-strips 324 are formed on the inside of bore 322, terminating at their inner ends at a circumferential band 326 of wick material.

In operation, swellable agent element 318 pushes the stack of layers from the mouth 314 as in Examples 1 and 2, but as each passive excipient layer reaches band 326, they are supplied with moisture from the band enabling expansion to drive the preceding active layer (and, ultimately itself) from the capsule. While either the active or the passive layers could be expanded in this way, it is preferable that the layer which is expanded is formulated to be substantially more hygroscopic than those which are not intended to be expanded within the capsule in this manner. If the swellable agent 318 is designed to expand more slowly that normal, and if the layers are packed correspondingly closer together, a more compact capsule can result for a given delivery profile.

It has been found that capsules of this design can be made to deliver their contents in a pulsatory or oscillatory fashion, even when a single homogeneous layer or slug of excipient is loaded in the capsule. In this way, an active agent, when mixed uniformly with the excipient, can be delivered to the body in a pulsatory fashion, though the pulses are not as clearly defined as in a layered device. Such capsules are obviously less costly to manufacture that those with layered stacks.

EXAMPLE 4

The preceding examples have all been active capsules. This example, illustrated in FIG. 5, is a passive capsule and can be employed to deliver a homogeneous excipient/drug formulation in a sustained or a pulsatory fashion, or non-homogeneous layered formulation in a pulsatory or multi-dose fashion.

The capsule 400 simply consists of an impervious polymeric casing 410 with a closed end 412, an open end 414 and a pattern of axial wick-strips 416 and circumferential wick-bands 418 formed on its inner surface. In this case, only two diametrically-opposed wick-strips 410 are employed and extend the full length of the capsule bore. The lateral dimension and thickness (i.e. the fluid-carrying capacity) of these strips is limited with respect to the bands and is designed to be a small traction (perhaps 1%) of the liquid imbibing capacity of the excipient layer opposite any band 418.

If the capsule is loaded with a layered stack of layers which alternate in their swellability, it is desirable that the more swellable layers be arranged opposite the bands 418. However, the capsule could be loaded with a homogeneous slug of a suitable excipient/drug mix. In operation, liquid is slowly imbibed by the layer of excipient adjacent the band 418 which is nearest the exposed surface of the stack or slug, with relatively little moisture being transferred from the portions of the strips 416 conducting that liquid and the layer of excipient which lies between the band in question and the exposed surface. Thus, pulsatory delivery can be achieved with a homogeneous slug, or and in a more pronounced manner, with a layered stack.

EXAMPLE 5

Referring to FIGS. 6a and 6b, the fifth example is that of a passive multi-dose device which has two stacks connected in series. This will result in a shorter device for a given number of doses and allow the more uniform dispensing of many doses.

Here, the casing 502 of capsule 500 is an open-ended cylinder divided diametrically along its length into to hemi-cylindrical chambers 504 and 506 by an integral web 512, one end (the inner end) of the casing and chambers being hermetically closed by an end-cap 508. Web 512 has an axial bore or tube 514 formed centrally therein, one end (the outer end) of tube 514 being sealed with plug 516 and the other end (the inner end) being sealed by a pip 518 formed in the centre of end-cap 50B. An axially-extending edge-wick strip 522 is formed on the inner surface of one hemi-cylindrical chamber so as to extend the full length of the casing. A second wick 524 is threaded into bore 514 so that its inner end extends into chamber 504 through an appropriate hole formed in web 512 and so that its outer end extends through an appropriate hole in web 512 near the outer end of casing 502. A third axially-extending wick-strip 508 is formed on the inner surface of chamber 506 to connect with the second wick 524.

In operation, both chambers are loaded with layered stacks (indicated by broken lines at 528 and 530) and sealed with plugs (shown in broken lines at 532 and 534), and the capsule is implanted in the patient. Water conducted down wick-strip 522 in chamber 504 causes the pulsatory expulsion of layers 528 until the chamber is empty. Whereupon, water is conducted via central wick 524 to wick 526 in chamber 506 and the process is repeated.

EXAMPLE 6

An alternative multi-chamber capsule construction is shown in FIG. 7. Here, the casing 602 has four chambers 604 separated by axial webs 606. A central bore 608 is provided at the junction of webs 606 and the inner ends of casing 602 and chambers 604 are jointly closed by an end-cap 610. In the centre of the outer wall of each chamber, a capillary tube 612 is formed and opens out at its inner end into its respective chamber, as shown at 614. Each chamber may therefore be adapted to operate substantially as described in Example 1.

EXAMPLE 7

Figure 8:
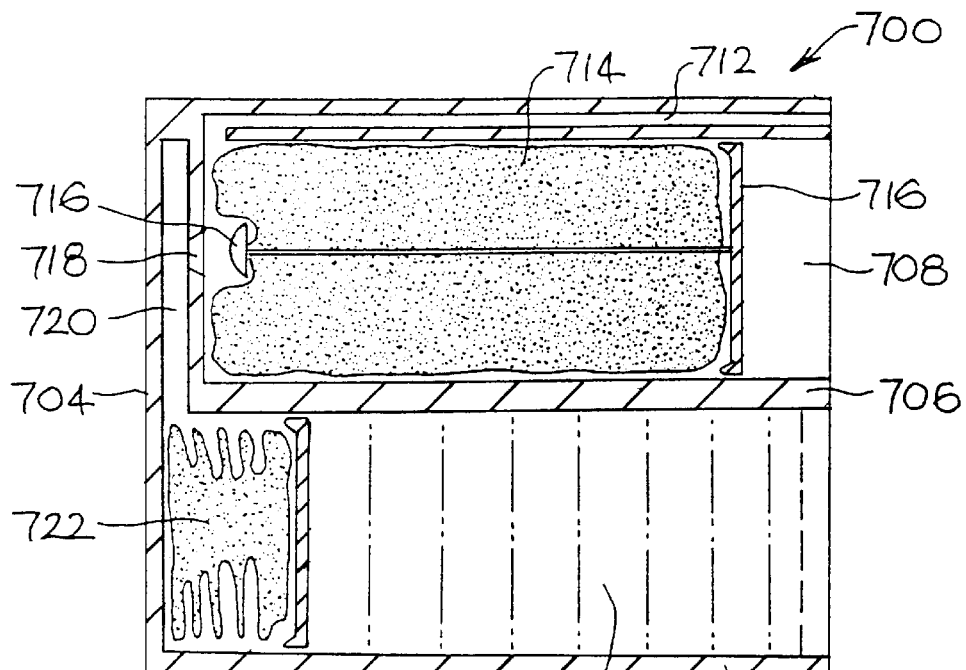
FIG. 8 is a longitudinal elevation of a multi-stage active device which comprises the seventh example of this invention.

This example (shown in FIG. 8) illustrates the application of the principles of the invention to a multi-stage active pulsatory capsule. Here, capsule 700 has an injection-moulded casing 702 with an integral end plate 704 and a central web 706 which divides the casing into two parallel cylindrical chambers 708 and 710. A capillary tube 712 is formed in the outer wall of chamber 708 so as to connect the exterior of the open end of capsule 700 to the bottom of chamber 704. A bagged swellable agent-element 714 (shown fully expanded) is located at the base of chamber 708 and receives its fluid from tube 712 (when implanted). Swellable agent element 714 includes an outer piston and an inner plug 716 (of smaller diameter than the piston), plug 716 normally closing a hole 718 in the base of chamber 708 which opens into a passage 720 that connects with the base of chamber 710. A bagged swellable agent 722 (shown unexpanded) is located at the inner end of chamber 710.

In operation, the chambers are loaded with their respective swellable agent-elements and stacked layers of excipient and drugs, making sure that plug 716 closes hole 718. The stacks in the chambers may be appropriately sealed. After implantation, liquid is conveyed via tube 712 to swellable agent 714 and the contents of chamber 708 are gradually discharged. When swellable agent 714 is fully extended, plug 716 is withdrawn from hole 718 and fluid is conveyed to swellable agent 722 so that the contents of chamber 710 are then gradually discharged.

EXAMPLE 8

This example illustrates the invention where the permeable fluid conveying passages are in the form of a plurality of pores.

Figure 9:
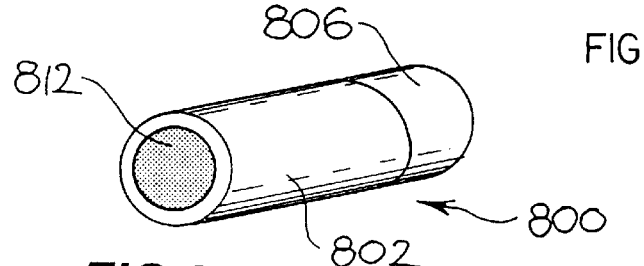
FIGS. 9 and 9A are a longitudinal and cross-sectional side view of a delivery device in accordance with the second preferred form of the invention as described in the eighth example.
Figure 9A:
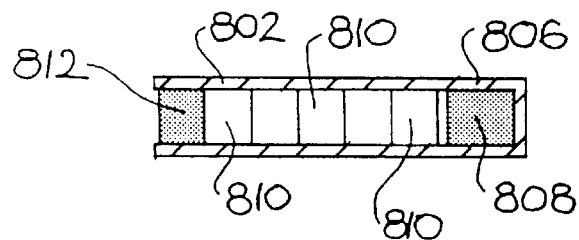

Referring to FIGS. 9 and 9A, the device 800 has a water impermeable wall 802 formed from non-porous polystyrene. The device has a closed end 806 formed from a porous polymer such as a porous polyethylene which surrounds a swellable material 808.

Figure 14B:
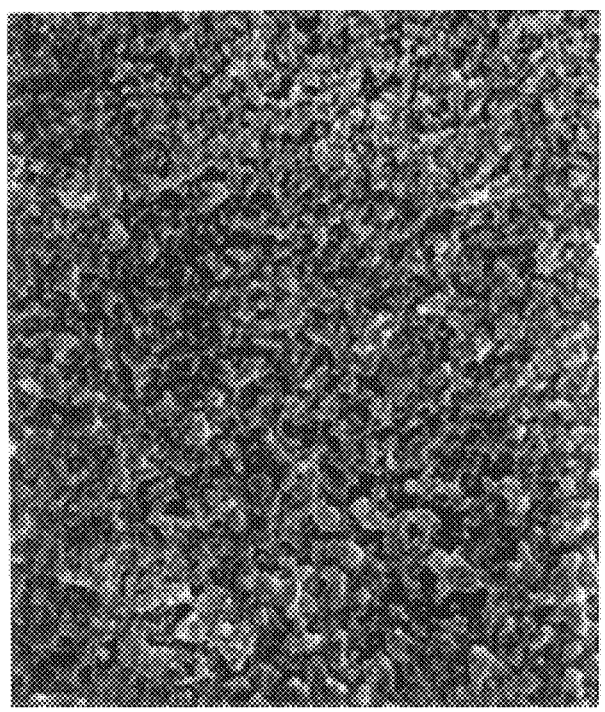

FIG. 14 shows scanning electron micrographs of the porous polyethylene (FIG. 14A) comparing it to a non-porous polystyrene (FIG. 14B).

A number of layers of biocompatible matrix containing bioactive layers 810 are positioned within the cavity formed by the impervious wall 802. The opening of the device may be closed with a biocompatible plug 812.

This device entails a combination of polymeric materials, one of which is porous and controls the entry of water to the driving system while the second is non-porous and protects the bioactive(s) from direct exposure to the environment, avoiding possible denaturation and premature release.

A number of devices having this arrangement were used to determine the factors affecting the rate of expansion of the driving system with time. In the test arrangement the bioactive containing layers were replaced by tablets without marker in an alternating series with tablets containing marker.

The hydrogel used in this embodiment is a polyacrylate-based hydrogel which is cast into (0.2×0.5 cm) cylindrical rods and placed into the above device in contact with the porous wall. Expansion of the hydrogel rod was measured with analytical callipers. For the swelling measurements, the devices were completely immersed in tubes containing 10 mL. of standard biological buffer (50 mM sodium potassium phosphate buffer, pH 7.5 at 37.5° C.) in a humid atmosphere of 5% $CO_2$. The ejection of tablets was monitored by measuring the absorption of buffer as marker was released from the tablet. The results are shown in FIG. 10 which demonstrates the swelling characteristics of the hydrogel and showing the rate of expansion of the swelling agent is reproducible (n=2).

IN VITRO STUDIES

An evaluation of the release of placebo tablets from the devices also suggested that in vitro ejection times are reproducible, thereby affording a device which may perform predictably in vivo.

An example of five similar release profiles are given in FIG. 11. This shows the change in absorbance with time. An examination of the profiles indicates that in four out of five tested devices, the first "pulse" was obtained on day 2 with a second "pulse" occurring at day 68 and subsequent "pulses" at days 20–24.

The release profile was affected by the hydrophylicity of the barrel. FIGS. 15 and B show the cumulative and daily release profiles respectively, of devices which were chemically treated with acrylic acid. Increased hydrophilicity of the barrel increased the ingress of water to the driving mechanism which in turn increases the number of pulses of active released compared to untreated devices observed over the same time interval.

IN VIVO STUDIES

Four of the five rats showed two distinct release profiles (FIG. 16). The fifth rat was noted to have a decrease in the amount of marker present in the urine but at no point ceased releasing the marker. The observed differences between the rats are due to small differences in the dimensions of the devices and possibly due to variations in the metabolic response of the rats to the marker.

FIGS. 12 and 13 show further embodiments of the invention.

Referring to FIG. 12, the device 110 comprises a housing formed from a cylindrical non-porous polymer portion 112 having an opening 114 and a cylindrical porous 116 polymer portion forming a closed end of the device. The porous portion of the housing is affixed to the non-porous portion by means of Loctite Prism™ adhesive or a cyano-acrylic ester based adhesive 118. This arrangement is suitable for the fabrication of an active swellable agent-driven device.

FIG. 13 shows an alternative arrangement wherein the housing 120 comprises a cylindrical non-porous polymer portion 122 having an open end 124 for dispensing the active agent and an annular portion 126 formed from a porous polymer located coaxially around the non-porous part and affixed thereto by means of Loctite Prism™ adhesive or a cyanoacrylic ester based adhesive 128. In this embodiment the porous polymer portion extends beyond the rear end of the non-porous polymer section, which does not extend to the full length of the device, to provide an outlet from the porous polymer to an active swellable agent located at the end of the device. A non-porous outer casing 129 is formed on the outside of the porous polymer.

Another form of delivery device in accordance with the invention depicted in FIG. 17 is prepared entirely from biocompatible materials. The device consists of a non-porous length of tubing 172 with a porous polymer or cap insert 174 at one end adjacent to a driving mechanism 175 which swells on contact with body fluids. The remaining length of tubing is packaged with alternating "active" tablets 176*a, b* and *c* incorporating lyophilised antigen and non-active spacer tablets 177*a* and *b*. A cap 178 may be used to prevent tablets from contacting the environment prior to use. Following implantation of the device, body fluids are imbibed, resulting in gradual swelling of the driving mechanism and subsequent expulsion of the tablets. Altering tablet size or the sequence of active/non-active tablets results in change in the profile of antigen release.

IN VITRO STUDIES

In vitro experiments were initially used to study the action of the device of FIG. 21. Biological marker tablets were prepared and packaged into devices which were then immersed in a gelatin-based media and incubated at 37° C. This media was prepared to mimic the physiological characteristics of body fluids, but was highly viscous in order to simulate the limited water availability of the in vivo environment. The media was changed daily, and assayed for marker content by spectrophotometry. Typical release profiles obtained from devices containing 4 marker tablets are shown in FIGS. 18A to D. As shown, 4 distinct peaks in dye release were observed. Improved fabrication techniques currently being developed are expected to reduce variability between devices.

IN VIVO TESTING

For initial in vivo testing of the delivery device prototype, sheep were obtained from a commercial source prior to first vaccination. A control group was immunised twice over a one month interval with liquid tetanus toxoid (Cyanamid-Webster) adjuvanted with aluminium hydroxide gel. The remaining sheep were implanted subcutaneously with delivery devices containing two tabletted doses of tetanus toxoid. No adjuvant was used in the preparation of the devices. Blood samples were collected at intervals and assayed for anti-tetanus antibody by ELISA. FIGS. 17A and B show the responses of individual animals from each group respectively, while FIG. 20 compares the mean responses of the two groups. Group mean anti-tetanus antibody responses determined following implantation of a pulsatile antigen delivery device containing two doses of tetanus toxoid (o), or injection of control sheep with two doses of liquid tetanus toxoid plus aluminium hydroxide adjuvant (□). The arrow indicates the time at which the secondary injection was administered to controls.

Arrows in FIG. 19A indicate estimated time of release of individual dosage units. Arrows in FIG. 19B indicate time of primary and secondary administration of liquid vaccine.

The primary responses of sheep which received the devices commenced 7 days post implantation, indicating that the first dose of antigen was immediately available, as animals vaccinated with the liquid toxoid responded in a similar time interval. The secondary response of the sheep which received the devices commenced approximately one week after the response of the control sheep was observed, indicating a period of 5 weeks was required for release of the second dose of tabletted antigen. There was no significant difference between either the primary or secondary responses of the control group and the group which received the implanted devices.

This indicates that the delivery device is capable of releasing antigen in a highly immunogenic form without the need for an adjuvant, producing antibody titres equivalent to those achieved through the use of the liquid toxoid preparation administered with aluminium hydroxide adjuvant.

Development of systems for single-shot immunisation would eliminate the need for multiple handling of stock, offering particular advantages to livestock industries. Although formulations are available which provide sustained release of antigen, such long exposure may induce antigenic tolerance, highlighting the need for a system which provides pulsatile, rather than continuous release. The use of microsphere combinations of varying size or hardness has recently being trialed in an effort to produce pulsatile antigen release profiles, however maintaining antigen stability has proved difficult and release of each dose generally occurs over an extended period, rather than in discrete, short-lived "pulses". In vitro experiments using the pulsatile antigen delivery device illustrated in FIG. 17 have shown that the "active" doses were released in a discrete pulses, while in vivo trials of prototype devices (FIGS. 18 and 20) have shown that antibody responses were induced to titres equivalent to those of control animals which received tetanus toxoid in a liquid form adjuvanted with aluminium hydroxide gel.

The devices of the invention may be in the form of miniaturised devices of single-unit construction, which is expected to reduce variability between devices. The device of FIG. 17 may be modified by replacement of the porous polymer cap with a porous inner plug, to give a device of constant diameter which may be administered by a handheld gun. The use of a handheld gun circumvents the requirement for surgery for implantation of the above embodiments. The preferred embodiment may be manufactured in the following way. A non-porous polymer, such as a heat shrinkable fluoroethylenepropylene (FEP), can be melted or compressed around a metal template adjacent to a porous polyethylene rope. After cooling, the metal template can be removed resulting in the manufacture of prototype devices comprising a non-porous, biocompatible, non-degradable housing closed by a fused porous rope of polyethylene at one end (FIG. 17A). This avoids the use of adhesives to link two very different materials together because heat is used to fuse the non-porous FEP with the porous polyethylene. Such a device is appropriate for subcutaneous delivery of vaccine as it is removed with the skin during carcass preparation. The device offers the advantage of being applicable to a wide range of antigens and release profiles, by changing the tablet formulations and the mode of packaging. The period of release may be altered by changing, the formulation of the driver tablet. In addition, the devices may incorporate other drugs, such as anthelmintics or antibiotics, making it suitable for delivery of multiple treatments in a single administration.

While a variety of examples of the application of the principles of the invention have been disclosed, those skilled in the art will appreciate that many more are possible without departing from these principles.

References

1. Eldridge, J. H., Staas, J. K., Chen. D., Marx, P. A., Tice, T. P. and Gilley, R. M. 1993. New advances in vaccine delivery systems. *Seminars in Haematology* 30 (4). Suppl. 4:16–25.

2. Morris, W., Steinhoff, M. C. and Russell, P. K. 1994. Potential of polymer microencapsulation technology for vaccine innovation. *Vaccine* 12:5–11.

3. Singh-Hora, M., Rana, R. K., Nunberg, J. H., Tice, T. R., Gilley, R. M. and Hudson, M. E. 1990. Controlled release of interleukin-2 from biodegradable microspheres. *Biotechnology* 8:755–758.

We claim:

1. A device for dispensing one or more active agents, the device including:

a housing having one or more openings;

an active agent or agents located within the housing;

a driving means located within, or at a closed end of, the housing, said driving means including an expandable material; and one or more fluid conveying passages adapted to convey fluid from outside the housing to the driving means; wherein said passages allow restricted but controlled conveyance of fluid, such as body fluid, to the expandable material but not so restricted as to provide semipermeable flow and further wherein in use said fluid leads to expansion of said expandable material with subsequent displacement of said active agent or agents and thus subsequent dispensing of said agent or agents.

2. A device according to claim 1 wherein the driving means includes an expandable layer of a passive or active agent and/or a liquid imbibing swellable material of an active agent.

3. A device according to claim 1 wherein the active agent is in a dosage form.

4. A device according to claim 1 wherein the device is adapted to provide continuous or pulsatile release, the housing is elongate and includes a multiplicity of layers arranged lengthwise therein with one or more layers being an expandable or non-expandable layer and one or more layers containing the active agent.

5. A device according to claim 4, wherein each active layer includes a protective skin or coating.

6. A device according to claim 1 wherein the housing is formed from a substantially liquid impermeable polymer selected from the group consisting of non-porous polyethylene, polycarbonate, polypropylene, polyvinyl chloride, polytetrafluoroethylene (PTFE), fluoroethylenepropylene (FEP), polyvinylidene fluoride (PVDF), polyvinylacetate, polystyrene, ethylene vinylacetate, nylon, polyurethane, a polyhydroxy alkoanate, silicone rubber, polysiloxane, polybutadiene, polyisoprene, poly(lactic acid), poly(glycolic acid), poly(alkyl 2-cyanoacrylates), polyanhydrides and polyorthoesters and mixtures thereof.

7. A device according to claim 6 wherein the housing of the device is formed from a hydrophobic biocompatible material and the internal walls of the housing or the fluid conveying passages are treated to render them hydrophilic.

8. A device according to claim 1 wherein the opening of the device is closed by an occlusion means formed of a material which is discharged, leached or eroded by the environment in which the device is to be used.

9. A device according to claim 1 wherein the driving means is a swellable hydrophilic polymer or hydrogel.

10. A device according to claim 9 wherein the driving means is selected from the group consisting of polyacrylates, poly(hydroxyalkyl methacrylates), polyvinyl alcohol, poly(N-vinyl-2-pyrrolidone), poly(vinyl acetate), poly(hydroxyethyl methacrylate), alginates, polyacrylamide, cellulose acetate phthalate, hydroxypropyl cellulose, carboxymethyl cellulose, ethyl cellulose, methyl cellulose, collagen, zein, gelatin, agarose, DEAE, Sephadex T, natural rubber, guar gum, gum agar, curdland or other schleroglucans, hydroxymethyl cellulose, albumin and mixtures thereof.

11. A device according to claim 1 wherein the fluid conveying passages permit blood vessels to infiltrate.

12. A device according to claim 1 wherein the fluid conveying passages have outlets which are located at one end of the housing adjacent to the expandable material.

13. A dispensing device for dispensing one or more active agents, the device including:

a housing having one or more openings;

an active agent or agents located within the housing;

a driving means located within or at a closed end of the housing, said driving means including an expandable material; and one or more capillary passages adapted to convey fluid from outside the housing to the driving means; wherein said passages allow restricted but controlled conveyance of fluid, such as body fluid, to the expandable material but not so restricted as to provide semipermeable flow and further wherein in use said fluid leads to expansion of said expandable material with subsequent displacement of said active agent or agents and thus subsequent dispensing of said agent or agents.

14. A device according to claim 13 wherein the device is adapted to provide pulsatile or continuous release including a multiplicity of layers arranged lengthwise in the housing with one or more layers being an expandable or non-expandable layer and one or more layers containing the active agent; and the capillary passages have outlets which are located against one or more of the expandable or non-expandable layers.

15. A device according to claim 14 wherein said expandable layers are formed with a radial skin which is relatively impervious to body fluid.

16. A device according to claim 13 wherein the capillary passages permit blood vessels to infiltrate.

17. A device according to claim 13 wherein the capillary passages extend along part or all of the housing such that an end of the passage or passages is located inside or close to an opening in the housing for ingress of fluid and another end of the passage or passages is located adjacent to the driving means for egress of the fluid from the passage.

18. A device according to claim 17 wherein the device further includes a shield-tube of larger diameter than the housing positioned around an outer end of the device, with the capillary passages being positioned within or adjacent to the outer wall of the housing.

19. A device according to claim 13 wherein the capillary passages include hydrophilic fibrous, granular mat-form or molecular wick material which facilitates the transport of water and aqueous solutions therethrough.

20. A device according to claim 19 wherein the capillary passages are extruded, intertwined or woven fibrous material in the form of a rope, cord or the like, the spacing between the fibres forming the capillary passages.

21. A device according to claim 20 wherein the fibres are formed from a hydrophilic polymeric material or a hydrophobic polymeric material with the surface thereof being treated so as to be hydrophilic.

22. A device according to claim 21 wherein the polymer fibres are formed from polyethylene, polyetheretherketone, polyimide, polytetrafluoroethylene, polyvinylidene fluoride, propylene or fluoroethylenepropylene.

23. A device according to claim 14 wherein one or more capillary channels are formed on the inner surface of the housing.

24. A device for dispensing one or more active agents, the device including:
    a housing having an opening and being formed at least in part from a substantially liquid impervious material;
    an active agent or agents located within the liquid impervious housing;
    a driving means located within, or at a closed end of, the housing, the driving means including an expandable material;
    said housing including a portion having a plurality of pores formed therein to convey fluid from outside the housing to the driving means, wherein in use said fluid leads to expansion of said expandable material with subsequent displacement of said active agent or agents and thus subsequent dispensing of said agent or agents.

25. A device according to claim 24 wherein the housing includes a porous plug, cover or cap associated with the body of the housing.

26. A device according to claim 24 wherein the housing includes a water impermeable section with an open end and a porous section fabricated from a porous polymer forming a closed end of the device and surrounding an expandable driving system.

27. A device for dispensing one or more active agents, the device including:
    a housing having an opening;
    at least one active agent located within the housing;
    a driving means located within, or at the closed end of, the housing, the driving means including an expandable material;
    one or more fluid conveying passages formed on the inner surface of the housing adapted to convey fluid from the outside of the housing to the driving means; and
    a constrained edge wick which extends the full length of the inner surface of the housing so that it contacts the edges of all layers in the stack loaded in the housing, the capacity of the edge wick to deliver water to each expanding layer being substantially less than the capacity of the layer to absorb water.

28. A device according to claim 27 wherein wick tracks are formed on the inner surface of the housing by printing a broad circumferential capillary band opposite each expandable active or spacer layer and by joining each band to the next by a fluid conveying passage.

29. A device according to claim 27 wherein said constrained edge wick extending the length of the inner surface of the housing is covered and enclosed with a layer of impermeable material so that it is adapted to convey water to only an end bearing a swellable agent.

30. A device according to claim 27 wherein said constrained edge wick extending the length of the inner surface of the housing is uncovered so that its inner face abuts the edges of the active layers when the housing is filled.

31. A device according to claim 27 wherein said constrained edge wick extending the length of the housing is left partially uncovered so that it abuts the edges of only selected layers.

32. A device according to claim 27 wherein said device includes a short wick formed in the inside of the outer end of the housing so as to contact and feed moisture to the edge of each expandable layer as it reaches the open end of the capsule.

33. A dispensing device for dispensing one or more active agents the device including:
    a housing having an opening;
    at least one active agent located within the housing;
    a driving means located within or at the closed end of the housing, the driving means including an expandable material;
    one or more capillary channels formed on the inner surface of the housing adapted to convey fluid from the outside of the housing to the driving means; and
    a constrained edge wick which extends the full length of the inner surface of the housing so that it contacts the edges of all layers in the stack in the housing, the capacity of the constrained edge wick to deliver water to each expanding layer being substantially less than the capacity of the layer to absorb water.

34. A device according to claim 33 wherein wick tracks are formed on the inner surface of the housing by printing a broad circumferential capillary band opposite each expandable active or spaces layer and by joining each band by a capillary passage.

35. A device according to claim 33 wherein said constrained edge wick extending the length of the inner surface of the housing is covered and enclosed with a layer of impermeable material so that it is adapted to convey water to only an end bearing a swellable agent.

36. A device according to claim 33 wherein said constrained edge wick extending the length of the inner surface of the housing is uncovered so that its inner face abuts the edges of the active layers when the housing is filled.

37. A device according to claim 33 wherein said constrained edge wick which extends the full length of the housing is left partially uncovered so that it abuts the edges of only selected layers.

38. A device according to claim 33 wherein said device includes a short wick formed in the inside of the outer end of the housing so as to contact and feed moisture to the edge of each expandable layer as it reaches the open end of the capsule.

* * * * *

UNITED STATES PATENT AND TRADEMARK OFFICE
CERTIFICATE OF CORRECTION

PATENT NO: 5,980,508

DATED: November 9, 1999

INVENTOR(S): Michael Cardamone, Herbert William Bentley

It is certified that error appears in the above-identified patent and that said Letters Patent are hereby corrected as shown below:

Column 13, line 47, "compared to 25" should be -- compared to 26 --.
Column 16, line 55, "wick-strips 410" should be -- wick-strips 416 --.
Column 16, line 59, "traction" should be -- fraction --.
Column 17, line 24, "end-cap 50B" should be -- end-cap 508 --.
Column 19, line 39, "cyanoacrylic" should be -- cyano-acrylic --.
Column 21, line 30, delete the comma after "changing".
Column 21, line 43, "T. P." should be -- T. R. --.

Signed and Sealed this

Third Day of April, 2001

Attest:

NICHOLAS P. GODICI

Attesting Officer

Acting Director of the United States Patent and Trademark Office